US011559554B2

(12) United States Patent
Ranganathan

(10) Patent No.: US 11,559,554 B2
(45) Date of Patent: Jan. 24, 2023

(54) MULTIFIBER PREBIOTIC COMPOSITION FOR DIGESTIVE HEALTH, WEIGHT CONTROL, BOOSTING IMMUNITY AND IMPROVING HEALTH

(71) Applicant: KIBOW BIOTECH, INC., West Chester, PA (US)

(72) Inventor: Natarajan Ranganathan, Broomall, PA (US)

(73) Assignee: KIBOW BIOTECH INC., Newtown Square, PA (US)

( * ) Notice: Subject to any disclaimer, the term of this patent is extended or adjusted under 35 U.S.C. 154(b) by 147 days.

(21) Appl. No.: 16/603,318

(22) PCT Filed: Apr. 10, 2018

(86) PCT No.: PCT/US2018/026798
§ 371 (c)(1),
(2) Date: Oct. 7, 2019

(87) PCT Pub. No.: WO2018/191206
PCT Pub. Date: Oct. 18, 2018

(65) Prior Publication Data
US 2020/0054690 A1 Feb. 20, 2020

Related U.S. Application Data

(60) Provisional application No. 62/602,085, filed on Apr. 10, 2017.

(51) Int. Cl.
| | | |
|---|---|---|
| A61K 35/42 | (2015.01) | |
| A61K 36/06 | (2006.01) | |
| A61K 31/716 | (2006.01) | |
| A61K 31/733 | (2006.01) | |
| A23L 33/14 | (2016.01) | |
| A23L 33/135 | (2016.01) | |
| A23L 33/21 | (2016.01) | |
| A61K 35/742 | (2015.01) | |

(52) U.S. Cl.
CPC .......... *A61K 35/742* (2013.01); *A23L 33/135* (2016.08); *A23L 33/14* (2016.08); *A23L 33/21* (2016.08); *A61K 31/716* (2013.01); *A61K 31/733* (2013.01); *A61K 36/06* (2013.01)

(58) Field of Classification Search
None
See application file for complete search history.

(56) References Cited

U.S. PATENT DOCUMENTS

2008/0199444 A1  8/2008  Cui

FOREIGN PATENT DOCUMENTS

| CN | 101926831 A | 12/2010 |
|---|---|---|
| CN | 101904417 B | 11/2012 |
| WO | 2016205394 A1 | 12/2016 |

OTHER PUBLICATIONS

Pandey, Kavita R; et al.; "Probiotics, prebiotics and synbiotics—a review" Journal of Food Science Technology, 52, 7577-7587, 2015 (Year: 2015).*
Kibow Fortis Product Information Sheet; https://kibowbiotech.com/pdfs/Kibow-Fortis-Product-Data-Sheet-Tablets.pdf (Year: 2015).*
Abhari, Khadijeh; et al; "The effects of probiotic, prebiotic and synbiotic diets containing Bacillus coagulans and inulin on rat intestinal microbiota" Iranian Journal of Veterinary Research, 16, 267-273, 2015 (Year: 2015).*
Jafarpour, Dornoush; et al; "Impact of synbiotic diets including inulin, Bacillus coagulans and Lactobacillus plantarum on intestinal microbiota of rat exposed to cadmium and mercury" Veterinary Science Development, 5:6061, 130-135, 2015 (Year: 2015).*
Abhari, Khadijeh; et al.; "The effects of prebiotic, probiotic and synbiotic diets containing Bacillus coagulans and inulin on serum lipid " Veterinary Science and Development, 5:5919, 95-98, 2015 (Year: 2015).*
Fitzpatrick, L.R., J.S. Small, W.H. Greene, K.D. Karpa and D. Keller (2011) "Bacillus Coagulans GBI-30 (BC30) Improves indices of Clostridium difficile-Induced colitis in mice," Gut Pathog. 3:16.
Garcia-Peris, P., C. Velasco, M.A. Lozano, Y. Moreno, L. Paron, C. de la Cuerda, I. Breton, M. Camblor, J. Garcia-Hernandez, F. Guamer and M. Hernandez (2012) "Effect of a mixture of inulin and fructo-oligosaccharide on Lactobacillus and Bifidobacterium intestinal microbiota of patients receiving radiotherapy: a randomised, double-blind, placebo-controlled trial," Nutr. Hosp. 27(6):1908-1915.
Grieshop, C.M., E.A. Flickinger and G.C. Fahey, Jr. (2002) "Oral Adminislialion of Arabinogalactan Affects Immune Status and Fecal Microbial Populations in Dogs," J. Nutr. 132:478-482.
Hun, L. (2009) "Original Research: Bacillus coagulans significantly improved abdominal pain and bloating in patients with IBS." Postgraduate Medicine 121(2):119-124.
International Preliminary Report on Patentability in PCT/US2018/026798 dated Oct. 15, 2019.
International Search Report and Written Opinion in PCT/US2018/026798 dated Jun. 11, 2018.
Kibow Biotech, Kibow Fortis, 2016 [Retrieved on May 29, 2018]. Retrieved from Internet: <URL:https://www.kibowbiotech.com/kibow-fortis/> entire document.
Kim, L.S., R.F. Waters and P.M. Burkholder (2002) "Immunological Activity of Larch Arabinogalactan and Echinacea: A Preliminary, Randomized, Double-blind, Placebo-controlled Trial. Alternative Medicine Review." 7(2):138-149.

(Continued)

*Primary Examiner* — David W Berke-Schlessel
(74) *Attorney, Agent, or Firm* — Licata & Tyrrell P.C.

(57) ABSTRACT

A composition composed of xylooligosaccharide, arabinogalactan, inulin, *Ganoderma lucidum* beta glucan, insoluble yeast β (1, 3/1, 6)-glucan, soluble oat β (1,3/1, 4)-glucan, and insoluble dried *Saccharomyces cerevisiae* fermentate, with a *Bacillus coagulans* component, for use in improving or maintaining digestive health, weight and glucose balance and boosting immunity is provided.

12 Claims, 17 Drawing Sheets

(56) References Cited

OTHER PUBLICATIONS

Kobayashi, T., M. Okazaki, S. Fujikawa and K. Koga (1991) "Effect of xylooligosaccharides on feces of men." Nippon Nogeikagaku Kaishi 65:1651-1653.
Mäkeläinen, H., S. Forssten, M. Saarinen, J. Stowell, N. Rautonen, A.C. Ouwehand (2010) "Xylo-oligosaccharides enhance the growth of bifidobacteria and Bifidobacterium lactis in a simulated colon model." Beneficial Microbes 1 (1):81-91.
Muralikrishna, G., S. Schwarz, G. Dobleit, H. Fuhrmann, and M. Krueger (2011) "Fermentation of feruloyl and non-feruloyl xylooligosaccharides by mixed fecal cultures of human and cow: a comparative study in vitro." Eur. Food Res. Technol. 232(4):601-661.
Othman, R.A., M.H. Moghadasian and P.J. Jones (2011) "Cholesterol-lowering effects of oat β-glucan." Nutrition Reviews 69(6):299-309.
Pourghassem, G.B., P. Dehghan, A. Aliasgharzadeh and M. Asghari Jafar-Abadi (2013) "Effects of High Performance Inulin Supplementation on Glycemic Control and Antioxidant Status in Women with Type 2 Diabetes." Diabetes and Metabolism Journal 37(2): 140-148.
Robinson, R.R., J. Feirtag and J.L. Slavin (2001) "Effects of dietary arabinogalactan on gastrointestinal and blood parameters in healthy human subjects." J. Am. Coll. Nutr. 20(4):279-285.
Tovar, A.R., M.C. Caamano, S. Garcia-Padilla, O.P. García, M.A. Duarte, J.L. Rosado (2012) "The inclusion of a partial meal replacement with or without inulin to a calorie restricted diet contributes to reach recommended intakes of micronutrients and decrease plasma triglycerides: a randomized clinical trial in obese Mexican women." Nutrition Journal 11:44.
Zhao, J. and P.C.K. Cheung (2011) "Fermentation of β-Glucans Derived from Different Sources by Bifidobacteria: Evaluation of Their Bifidogenic Effect," J. Agric. Food Chem. 59(11):5986-5992.
Extended European Search Report dated Jan. 13, 2021 for EP 18784991.4, filed Apr. 10, 2018.
Patel, et al. (2015) "New approaches for bacteriotherapy: probiotics, new-generation probiotics, and synbiotics," Clinical Infectious Diseases 60(2)S108-S121.

* cited by examiner

MULTIFIBER PREBIOTIC COMPOSITION FOR DIGESTIVE HEALTH, WEIGHT CONTROL, BOOSTING IMMUNITY AND IMPROVING HEALTH

This application is a U.S. National Stage Application of PCT/US2018/026798 filed Apr. 10, 2018 and claims the benefit of priority to U.S. Provisional Application Ser. No. 62/602,085 filed Apr. 10, 2017, the contents of each of which are incorporated herein by reference in their entirety.

BACKGROUND

Stress, diet, lifestyle choices and regular use of antibiotics and other drugs contribute to altering the microflora the body needs to maintain healthy digestion, to fight illness and disease, and to make sure the body gets all the nutrients it needs.

Prebiotics are defined as "selectively fermented ingredients that allow specific changes, both in the composition and/or activity in the gastrointestinal flora that confer benefits upon host well-being and health" (Roberfroid (2007) *J. Nutr.* 137 (3 Suppl. 2):830S-7S; Gibson & Roberfroid (1995) *J. Nutr.* 125:1401-12). Prebiotics occur naturally in a variety of foods, especially high-fiber foods, including certain fruits, vegetables and grains. Prebiotics are sometimes known as fermentable fiber. They are composed mainly of oligosaccharides, sugar molecules and soluble fiber.

Not all dietary carbohydrates are prebiotics. The criteria for classification as a prebiotic includes resistance to gastric acidity, to hydrolysis by mammalian enzymes, and to gastrointestinal absorption; fermentation by intestinal microflora; and selective stimulation of the growth and/or activity of those intestinal bacteria that contribute to health and well-being (Gibson & Roberfroid (1995) supra).

The health benefits of dietary fibers are now well-established. Fiber has a role to play in gut health. Higher intakes have been linked to health benefits such as lowering body weight, reducing inflammation, and reducing blood cholesterol levels. When dietary fibers are metabolized by gut microbiota, short-chain fatty acids (SCFAs) are produced which can dampen inflammatory pathways in macrophages and dendritic cells (DCs), promote the development of regulatory T (Treg) cells and maintain intestinal integrity and health. The SCFAs produced reduce fecal and colonic pH, provide energy for colonocytes and modulate the gut microbiota.

In addition to beneficial effects of prebiotic dietary fibers, probiotics have also been shown to promote gastrointestinal health (Pandey, et al. (2016) *J. Food. Sci. Technol.* 52:7577-7587; Li, et al. (2016) *Biotechnol. Adv.* 34:1210-1224). As a result, recent research has examined the role of prebiotics and probiotics together on overall health. In addition to the production of SCFAs and the potential direct benefits of the increased fiber intake, gut microbiome composition has been shown to be modulated by prebiotics (Pandey, et al. (2016) *J. Food. Sci. Technol.* 52:7577-7587; Li, et al. (2016) *Biotechnol. Adv.* 34:1210-1224). Lactobacilli and Bifidobacteria, the two main dominant groups of bacteria which reside in the colon, are considered probiotics and are known to be beneficial to human health. Recent studies have implicated their role beyond gut and digestive health, however, including a link between gut microbiome and neurological diseases such as autism and a variety of mood disorders (Li, et al. (2016) *Biotechnol. Adv.* 34:1210-1224). Secondly, as we grow older the bifidobacteria population in our gut decreases and thus needs to be replenished. It is important to maintain levels of these beneficial microbes in sufficient numbers to promote overall good health.

Xylooligosaccharides are soluble oligomers of xylan that are derived from hemicellulose of plants. In studies using a simulated colon system, the growth of bifidobacteria was increased in the presence of the prebiotic xylooligosaccharide (Makelainen, et al. (2010) *Benefic. Microbes* 1(1):81-91). It has been found as well that feeding xylooligosaccharide to human subjects increases the bifidobacteria population in gut (Kobayashi, et al. (1991) *Nippon Nogeikagaku Kaishi* 65:1651-1653). Increases in lactobacilli and bifidobacteria colonies were reported in fecal cultures when xylooligosaccharide was added (Muralikrishna, et al. (2011) *Eur. Food Res. Technol.* 232:601-61). These studies show that xylooligosaccharide has beneficial effects on the gut microbiome.

Arabinogalactan is a natural soluble polysaccharide that is present in a wide variety of plants like carrots, wheat, radishes and peas. Arabinogalactan is fermentable by the gut microbiome and is considered to be a prebiotic dietary fiber (Robinson, et al. (2001) *J. Am. Coll. Nutr.* 20:279-285; Grieshop, et al. (2002) *J. Nutr.* 132:478-482). Arabinogalactan has been shown to have immunomodulatory activity. It was shown to activate human peripheral blood mononuclear cells (PMBC) to release gamma interferon which stimulated Natural Killer cell activity, and to reduce the incidence of upper respiratory infections.

Inulin is a natural storage carbohydrate present in a large number of plants such as chicory, leeks, burdock, Jerusalem artichoke and onions. In the colon, inulin is rapidly fermented by the residing microbes to form SCFAs, which are beneficial to colon health. Inulin has prebiotic activity as well to stimulate the growth of lactobacteria and bifidobacteria, and reducing the number of pathogenic bacteria. Studies with diabetic rats showed that when administered orally, inulin could reduce blood lipid and glucose (Byung-Sung, et al. (2011) *J. Anim. Vet. Adv.* 10:2501-2507). Inulin has also shown anti-cholesterolemic effects in human studies and linked to reducing the risk of colon cancer. Modulating the gut microbiota in obesity using prebiotics like inulin and probiotics also has been studied (Backhed, et al. (2011) *Nat. Rev. Endocrinol.* 7:639-646).

Oat bran is a well-known dietary fiber. Beta glucans derived from oats has been tested for its cholesterol lowering ability (Othman, et al. (2011) *Nutr. Rev.* 69:299-309). Oat bran has been linked to beneficial effects in diabetes, cardiovascular disease and immunity (Cheickna & Zhang (2012) *Compre. Rev. Food Sci. Food Safety* 11:355-365).

Beta glucans have been gaining prominence in their role for boosting immunity, in particular those derived from medicinal mushrooms. The beta glucans are glucose polymers and constitute the cell walls of yeast and mushrooms. Beta glucans activate macrophages to boost immunity and have been well studied for their immune stimulation property and potential anti-carcinogenic effects (Huang & Ning (2010) *Int. J. Biol. Macromol.* 47:336-341; Thyagarajan, et al. (2006) *Int. J. Mol. Med.* 18:657-64; Yu, et al. (2007) *J. Food Sci.* 72:S435-442). It has been reported that three different *Bifidobacterium* species, *B. infantis*, *B. longum* and *B. adolescentis* could grow on beta glucans and produce SCFAs. In a study in humans, beta glucan from *Agaricus* mushroom reduced levels of inflammatory cytokines in patients with ulcerative colitis and Crohn's disease.

Baker's yeast (*Saccharomyces cerevisiae*) whole cells contain many immune supporting compounds and metabolites. It is a whole food, and various human trials have shown that this yeast has immune boosting properties (Moyad, et al. (2010) *J. Alternat. Comple. Med.* 16:213-218; Moyad, et al. (2009) *Adv. Ther.* 26:795-804; Jensen, et al. (2011) *J. Medic. Food* 14:1002-1010). In a rat immune model, administration of a fermentate of yeast prevented and reduced inflammation.

*Bacillus coagulans* is another probiotic organism that has gained attention and is commonly found in products sold commercially. Administration of *B. coagulans* has been shown to have beneficial effects in patients with *Clostridium difficile*-associated disease.

DESCRIPTION OF THE DRAWINGS

FIG. 9A), transverse colon (TC; FIG. 9B), and descending colon (DC; FIG. 9C) assessed with qPCR. Each bar represents the averaged copy numbers over the control and treatment period.

SUMMARY OF THE INVENTION

Figure 1:
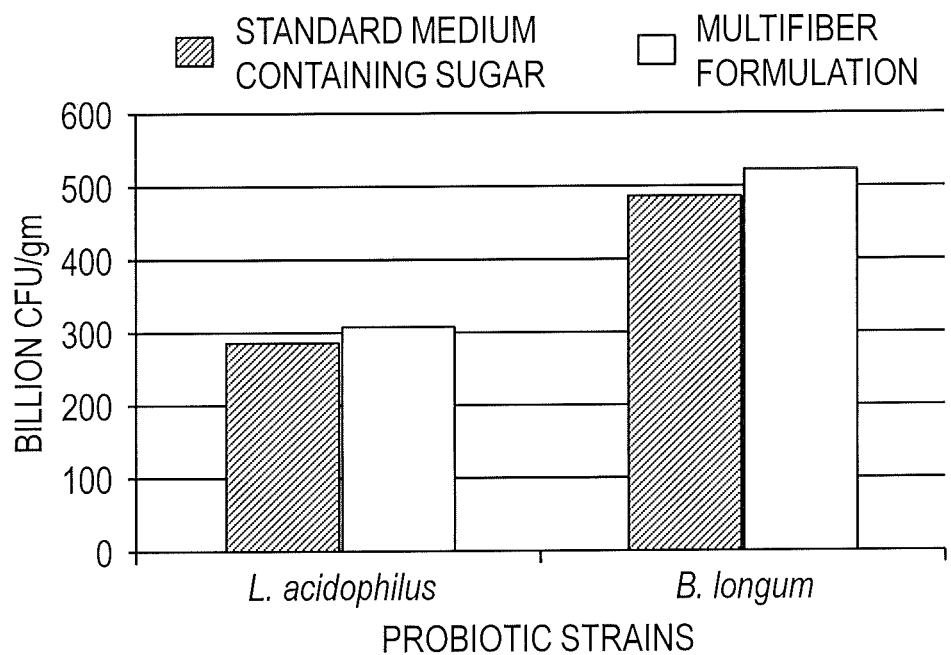
FIG. 1 depicts the effect of the multifiber formulation of the present invention on in vitro growth of *Lactobacillus acidophilus* and *Bifidobacterium longum*.

The present invention is a composition comprising, or consisting essentially of, xylooligosaccharide, arabinogalactan, inulin, *Ganoderma lucidum* beta glucan, insoluble yeast β (1, 3/1, 6)-glucan (e.g., *S. cerevisiae* β (1, 3/1, 6)-glucan), oat β (1, 3/1, 4)-glucan, insoluble dried *Saccharomyces* cerevisiae fermentate, and the probiotic *Bacillus coagulans*. In yet other embodiments, the formulation includes at least one excipient. In some embodiments, the composition takes the form of a food product, dietary supplement, comestible medical food, pharmaceutical product, or nutraceutical product. A method for improving or maintaining digestive health, weight, glucose balance and boosting immunity using said compositions is also provided.

DETAILED DESCRIPTION OF THE INVENTION

Apart from digestive health, which is a concern due to the changing lifestyle and dietary habits, other human health concerns arising include weakened immunity, obesity and high cholesterol levels, as well other metabolic disorders. Low dietary fiber intake is associated with increased risk of obesity, cardiovascular disease and type 2 diabetes among others (Cho, et al. (2013) *Am. J. Clin. Nutr.* 98:594-619; Liu, et al. (2003) *Am. J. Clin. Nutr.* 78:920-927; Trock, et al. (1990) *J. Natl. Cancer Inst.* 82:650-61; Ludwig, et al. (1999) *JAMA* 282:1539-1546). It is believed that dysbiosis, or imbalance of the microbiome, alters the metabolites produced by gut bacteria, which in turn may dysregulate innate and adaptive immune responses, and eventually lead to inflammation and/or loss of protection against infection. Certain gut bacteria can produce toxins, such as ammonia, D-lactate, endotoxin (lipopolysaccharide), and exotoxin (enterotoxin), which can further aggravate intestinal lesions. Whole genome sequencing of fecal samples revealed that there was a shift in the Bacteroidetes: Firmicutes ratio with fiber consumption (Holscher, et al. (2015) *Am. J. Clin. Nutr.* 101:55-64), showing the impact of dietary fiber on the phylogenetic structure and functional capacity of the fecal microbiome of healthy adults.

Some dietary fibers also have the ability to stimulate the growth of beneficial bacteria (probiotic bacteria) in the colon, also known as "prebiotic" activity. Commercially available fibers are mainly formulated for digestive health and include products such as BENEFIBER® (dietary fiber supplement; Novartis AG), METAMUCIL® (dietary supplement; Proctor & Gamble Co.) and CITRUCEL® (Laxative; Merrell Dow Pharmaceuticals, Inc.) dietary fiber available from Glaxo Smith Kline. These commercially available products, however, are made up of only one kind of fiber. In the present invention, a multiple fiber (both soluble and insoluble) product has been developed which can be used to address various health concerns and also restore gut microflora balance by working as a prebiotic.

It has now been found that a mixture of prebiotic and probiotic components in an oral formulation has beneficial health effects that include improving and maintaining digestive health, maintaining a healthy weight, improving glucose control, and boosting immunity. More specifically, a particular combination of soluble and insoluble prebiotics has now been identified for use in enhancing the growth of beneficial microorganisms native to the human intestine (e.g., *Lactobacillus* and *Bifidobacterium* species), and in providing positive effects to improve health. Given the beneficial roles of the intestinal microbiota in the human health and preventative potential in diseases including autoimmune diseases, colon cancers, gastric ulcers, cardiovascular disease, chronic kidney disease, functional bowel diseases and obesity, the present composition finds application in maintaining digestive health, weight control and glucose balance. In addition, the combination of soluble and insoluble prebiotics has been combined with the probiotic *B. coagulans* to provide a composition for not only enhancing the growth of beneficial microorganisms native to the human intestine (e.g., *Lactobacillus* and *Bifidobacterium* species), but also for boosting immunity in a subject. The composition of the present invention comprises or consists of xylooligosaccharide, arabinogalactan, inulin, *Ganoderma lucidum* beta glucan, insoluble yeast β (1, 3/1, 6)-glucan, oat β (1, 3/1, 4)-glucan, insoluble dried *S. cerevisiae* fermentate, and *B. coagulans*.

Given that the instant compositions include both soluble fibers, which balance intestinal pH and remove toxic waste, and insoluble fibers, which bind fatty acids, lower total cholesterol and regulate blood sugar, the composition of this invention has a variety of activities including anti-carcinogenic, anti-microbial, hypolipidemic, immune boosting, and glucose modulatory activities. Further, this prebiotic composition can improve mineral absorption and balance, and stimulate the growth of bacteria belonging to the *Bifidobacterium* and *Lactobacillus* families. Pharmacokinetically, the prebiotic and probiotic components of this invention reach the colon largely intact.

Xylooligosaccharide, or XOS, refers to a soluble, nondigestible sugar polymer composed of two to seven xylose molecules bonded with β (1, 4) glycosidic bonds. Xylooligosaccharide is present in fruits, vegetables, bamboo, honey and milk and is produced by enzymatic hydrolysis of xylan-rich food ingredients, such as corncob, corn bran, rice bran, wheat bran, and *psyllium* with endoxylanase. Accordingly, the xylooligosaccharide of this invention is obtained by enzymatic digestion of larger carbohydrate molecules. Xylooligosaccharide can also be obtained from commercial sources (e.g., Hangzhou, China).

Since Xylooligosaccharides resist digestion in the upper gastrointestinal tract, they are able to function in the large intestine to increase the growth of *Bifidobacterium* species (JP 2003048901), thus improving gastric function. In addition, xylooligosaccharides have the potential to improve blood sugar levels and fat metabolism, restore normal intestinal flora following antibiotic, chemo, or radiation therapies, increase mineral absorption and vitamin B production, and reduce intestinal putrification. In animal models, XOS has also been shown to decrease triglycerides (Beylot (2005) *Br. J. Nutr.* 93 (suppl 1) S163-8). Along with FOS, XOS was shown to reduce the number of aberrant crypt foci in the colon of 1, 2-dimethylhydrazine-treated male Sprague-Dawley rats (Hsu, et al. (2004) *J. Nutr.* 134:1523-8). Studies using a simulated colon system have shown that it is possible to increase the growth of bifidobacteria using XOS as a prebiotic (Makelainen, et al. (2010) *Beneficial Microbes* 1:81-91). It has been reported that that feeding XOS to human subjects increased the Bifidobacteria population in colon (Okazaki, et al. (1990) *Bifidobacteria Microflora* 9:77-86). Similar results were reported in a population of Japanese men (Kobayashi, et al. (1991) *Nippon Nogeikagaku Kaishi* 65:1651-1653). Increased levels of lactobacilli and bifidobacteria were observed in fecal cultures with added XOS (Muralikrishna, et al. (2011) *Eur. Food Res. Technol.* 232:601-61). Considered together, these studies demonstrated that XOS exposure had a positive impact on growth of beneficial microbes. The safety of XOS for use in humans is demonstrated by its recognition as a Generally Regarded as Safe (GRAS) substance by the U.S. Food and Drug Administration (FDA).

Arabinogalactan is a water-soluble β (3, 6)-D-galactan made up of arabinose and galactose in a ratio of 1:6. It is present in a wide variety of plants like carrots, wheat, radishes and peas. Arabinogalactan is an immunomodulator, which has been shown to activate human peripheral blood mononuclear cells (PMBC) to release proinflammatory cytokines and stimulate NK cell activity (Hauer & Anderer (1993) *Cancer Immunol. Immunother.* 36:237-44; Riede, et al. (2013) *Curr. Med. Res. Opin.* 29:251-8). Arabinogalactan has been shown to impact the immune system in a positive manner, i.e., boosting immunity (Riede, et al. (2013) *Curr. Med. Res. Opin.* 29: 251-258).

For dietary consumption, arabinogalactan is isolated from the wood of the larch tree (*Larix* species) and is approved for use as a dietary fiber by the U.S. Food and Drug Administration (FDA). Larch arabinogalactan, which is fermentable by gut bacteria (Robinson, et al. (2001) *J. Am. Coll. Nutr.* 20:279-85; Grieshop, et al. (2002) *J. Nutr.* 132:478-82), is approximately 98% arabinogalactan having a galactan backbone that features $\beta(1,3)$ linkages and galactose $\beta(1,6)$ and arabinose $\beta(1,6$ and $1,3)$ sugar side chains.

Arabinogalactan can be isolated and/or purified by conventional methods. For example, arabinogalactan can be extracted with aqueous medium (e.g., pure water or water with minor amounts of dissolved compounds such as organic acids or surface-active agents that promote extraction) from the lumen of cells found in the Western and Eastern Larch trees known respectively as *Larix occidentalis* and *L. laricina*. See, e.g., U.S. Pat. No. 3,509,126. Another source of Arabinogalactan is from *Tinospora cordifolia*, a glabrous, succulent, climbing shrub native to India. Alternatively, arabinogalactan can be obtained from commercial sources (e.g., MAYPRO INDUSTRIES, Purchase, N.Y.).

Inulin is a water-soluble dietary fiber composed of oligofructose with a terminal glucose molecule. It is obtained from Jerusalem artichoke (*Helianthus tuberosus*), chicory roots and agave. Several methods for inulin extraction from Jerusalem artichoke have been developed. For example, Jerusalem artichoke tubers can be mixed with hot water (Yamazaki, et al. (1994) *J. Sci. Food Agri.* 64:461-5), with or without a pretreatment step involving boiling water extraction for 10-15 minutes (U.S. Pat. No. 5,968,365). Inulin can also be obtained from commercial sources, e.g., MAYPRO INDUSTRIES (Purchase, N.Y.), which is an organic powder composed of at least 90% inulin and less than 7% fructose, less than 3% glucose, less than 2% sucrose and less than 1% other carbohydrates.

Inulin is a prebiotic that supports the growth of lactobacteria and bifidobacteria (Garcia-Peris, et al. (2012) *Nutr. Hosp.* 27:1908-15) and reduces blood lipid and glucose (Byung-Sung, et al. (2011) *J. Anim. Vet. Advance* 10:2501-7). Inulin has also shown anti-cholesterolemic effects in human studies (Letexier, et al. (2003) *Am. J. Clin. Nutr.* 77:559-64) and exhibited a role in reducing colon cancer (Pool-Zobel, et al. (2005) *Br. J. Nutr.* 93:s73-s90).

*Ganoderma lucidum* beta glucan is used herein to refer to a water soluble carbohydrate polymer derived from the mycelium of *Ganoderma lucidum*. In particular, the *G. lucidum* beta glucan of this invention is short $\beta$ (1, 6) branches coming off of a $\beta$ (1, 3) backbone. In certain embodiments, the beta glucan has a molecular weight in a range from 35000 to 2000000 Da. Research has demonstrated that this mushroom beta glucan effectively supports the immune system by activating the front line immune cells to support a healthy and robust immune response without over-stimulating it. Beta glucan enhances the immune response by activating the macrophages, which consume foreign invaders and "trigger" other components of the immune system including Granulocytes (Neutrophil, Eosinophils, and the Basophils), B- and T-cells, and Natural Killer (NK) cells to deal with the other potential threats.

Beta glucan can be obtained by culturing *G. lucidum* in trehalose and mannose according to known methods (see, e.g., US 2009/0098619) and subsequently extracting and purifying the beta glucan by conventional methods, e.g., boiling water extraction or ethanol precipitation (see, e.g., US 2014/0031542). Alternatively, purified *G. lucidum* beta glucan can be obtained from commercial sources. An exemplary mushroom beta glucan is IMMUNLINK MBG (carbohydrate polymer containing mushroom beta glucan) available from Super Beta Glucan Inc. (Irvine, Calif.).

Insoluble yeast $\beta(1,3/1,6)$-glucan is used herein to refer to insoluble beta glucan from yeast composed primarily of $\beta(1,3)$-linked glucose molecules with periodic $\beta(1,3)$ branches linked via $\beta(1,6)$ linkages and is more formally known as poly-(1,6)-$\beta$-D-glucopyranosyl-(1,3)-$\beta$-D-glucopyranose. The source of insoluble yeast $\beta(1,3/1,6)$-glucan can be from yeast cells of any strain of yeast, including, for example, *Saccharomyces cerevisiae, S. delbrueckii, S. rosei, S. microellipsodes, S. carlsbergensis, S. bisporus, S. fermentati, S. rouxii, Schizosaccharomyces pombe, Kluyveromyces polysporus, Candida albicans, C. cloacae, C. tropicalis, C. utilis, Hansenula wingei, H. arni, H. henricii, H. americana, H. canadiensis, H. capsulata, H. polymorpha, Pichia kluyveri, P. pastoris, P. polymorpha, P. rhodanensis, P ohmeri, Torulopsis bovin*, and *T. glabrata*. The yeast cells may be cultured by methods known in the art. Typical growth media include, for example, glucose, peptone and yeast extract. The yeast cells may be harvested and separated from the growth medium by methods typically applied to separate the biomass from the liquid medium. Such methods typically employ a solid-liquid separation process such as filtration or centrifugation. Preferably, the cells are harvested in the mid-to-late logarithmic phase of growth, to minimize the amount of glycogen and chitin in the yeast cells. In this respect, the insoluble yeast $\beta$ (1, 3/1, 6)-glucan has a glucan content of greater than 50% glucan. In certain embodiments, the remainder can be composed of intracellular lipids and/or glycogen.

Preparation of insoluble yeast beta glucan can involve treating the yeast with an aqueous alkaline solution at a suitable concentration to solubilize a portion of the yeast and form an alkali-hydroxide insoluble beta glucan preparation having primarily $\beta(1,6)$ and $\beta(1,3)$ linkages. The alkali generally employed is an alkali-metal hydroxide, such as sodium or potassium hydroxide or an equivalent. In certain embodiments, it is desirable to remove substantially all of the protein material from the cell, e.g., by mild acid treatment. Such removal is carried out to such an extent that less than one percent of the protein remains with the insoluble beta glucan. The insoluble beta glucan can be, if necessary or desired, subjected to further washings and extraction to reduce the protein and contaminant levels. After processing the product pH can be adjusted to a range of about 6.0 to about 7.8. See, e.g., US 2006/0009419 and U.S. Pat. No. 5,849,720 for extraction methodology. Insoluble yeast beta glucans can also be obtained from commercial sources, e.g., MAYPRO Beta Glucan (MAYPRO INDUSTRIES, Purchase, N.Y.). In some embodiments, the beta glucan is modified by chemical treatment with an acid (e.g., acetic acid) to decrease the amount of $\beta$ (1, 6) linkages and thus, change the hydrodynamic properties of said glucans as evidenced by an increase in the viscosity of aqueous solutions of these modified glucans.

Soluble oat $\beta$ (1, 3/1, 4)-glucan refers to a linear polysaccharide composed mainly of (1, 3)-linked cellotriosyl and cellotetraosyl units (>90%) that is obtained from common oat (*Avena sativa*). Oat $\beta$ (1, 3/1, 4)-glucan has been shown to possess cholesterol lowering activity (Othman, et al. (2011) *Nutr. Rev.* 69(6):299-309) and provide a beneficial role in diabetes, cardiovascular diseases, and immunity (Daou & Zhang (2012) *Comp. Rev. Food Sci. Food Safety* 11:355-365). Extraction methodologies for obtaining oat β(1,3/1,4)-glucan are based on the solubility of β-glucan in hot water and in alkaline solutions, separation of the dissolved proteins by isoelectric precipitation, and precipitation of the β-glucan by ammonium sulfate, 2-propanol, or ethanol (Wood, et al. (1978) *Cereal Chem.* 55:1038-49). The yield from oat bran was higher, 61%, and the separated fraction contained 84% beta-glucan. A similar method has been used to extract oat beta-glucan, with subsequent purification by dialysis, ultrafiltration, or alcohol precipitation (Beer, et al. (1996) *Cereal Chem.* 73:58-62). It was possible to produce preparations with beta-glucan content of 60%-65% using the above-referenced methods. In certain embodiments, the oat beta glucan used in accordance with the present invention includes between 20% and 40% beta-glucan. Oat β(1,3/1,4)-glucan can also be obtained from commercial sources, e.g., OATWELL 22 oat beta glucan (DSM Nutritional Products, Inc., Heerlen, The Netherlands), which is composed of 21 to 23% beta-glucan.

Insoluble dried *S. cerevisiae* fermentate refers to the inactive whole yeast cell of *S. cerevisiae* and the natural fermentative byproducts that are created by the fermentation of the yeast cells. Therefore, dried fermentate is not solely a brewer's yeast, active yeast, or isolated beta-glucan. Dried fermentate can be obtained by traditional fermentation, which requires a food grade yeast strain of *S. cerevisiae* in media containing water, a nitrogen source, a carbon source, and micronutrients. After the prescribed fermentation period, the entire wet product (i.e., yeast cells in the media) is placed in a dryer for dehydration. Dehydration is done at a temperature necessary to kill the yeast cells. Subsequently, the product is milled and used in the instant composition. Dried *S. cerevisiae* fermentate can also be obtained from commercial sources, e.g., EPICOR dried *S. cerevisiae* fermentate (Embria Health Sciences, Ankeny, Iowa).

Beta glucans are glucose polymers composed of various beta linkages (e.g., 1, 3; 1, 4; 1, 6) and constitute the cell walls of yeast (e.g., *S. cerevisiae*), yeast-like fungi (e.g., *Aureobasidium pullulans*) and mushrooms (e.g., *Lentinula edodes* (Shiitake), *G. lucidum* (Reishi)). They activate the complement system and enhance the macrophage and natural killer cells thus boosting immunity. Fermentation of beta glucans from, e.g., mushroom and barley, by three different *Bifidobacterium* species has been assessed (Zhao & Cheung (2011) *J. Agric. Food. Chem.* 59:5986-5692) and it was found that *B. infantis, B. longum* and *B. adolescentis* could grow on these beta glucans and produce short chain fatty acids (SCFA). Further, it has been demonstrated that yeast-derived beta glucans can decrease total plasma cholesterol in human studies (Nicolosi, et al. (1999) *Am. J. Clin. Nutr.* 70:208-212). Other human clinical trials show the beneficial effects of yeast beta glucan consumption in allergic rhinitis (Kirmaz, et al. (2005) *Eur. Cyto. Network* 16:128-134), breast cancer (Demir, et al. (2007) *Int. Immunopharmacol.* 7:113-116) and IL-10 levels in overweight human (Kohl, et al. (2009) *Nutr. Res.* 29:248-254).

In addition to the soluble and insoluble fiber components, the composition of prebiotics has added to it a probiotic organism, *B. coagulans*. Most of the probiotic bacteria belong to the class of Lactobacilli and Bifidobacteria. These bacteria are sensitive to temperature and, products or supplements containing these organisms must be stored under refrigerated conditions. This problem can be overcome using the spore forming Lactobacilli renamed as *Bacillus coagulans*. It is well studied and characterized and is considered to carry the status of Generally Recognized as Safe (GRAS). Human studies have shown that *B. coagulans* can reduce viral infection (Baron, (2009) *Postgrad. Med.* 121: 114-118), help patients with irritable bowel syndrome (Hun (2009) *Post grad. Med.* 121:119-124), and reduce inflammation (Jenson, et al. (2010) *BMC Immunol.* 11:15). The *B. coagulants* composition was 1.0 billion to 5.0 billion CFU/gm (Nebraska cultures, Walnut Creek, Calif.).

The composition of the present invention can be prepared as a food product, dietary supplement, comestible medical food, pharmaceutical product, or nutraceutical product. For the purposes of the present invention, a food product includes, but is not limited to, a health bar, health drink, yogurt, dahi, ice cream, frozen yogurt or other frozen food products. In certain embodiments, the fibers of the prebiotic composition are provided as micronized or powder formats. The ingestion of said product provides the instant prebiotics to the gut thereby enhancing the growth of beneficial microorganisms native to the human intestine (e.g., lactobacilli and *Bifidobacterium* species). In this respect, repeated ingestion of the product will have a highly beneficial effect upon the intestinal microflora by localization and colonization in the large intestine of microbes known to promote a healthy intestinal microenvironment.

In addition to prebiotics and probiotics, the compositions of the present invention can further contain various excipients, bulking agents, binders, sweeteners, flavors and/or additives. Optional excipients of the present composition include, without limitation, lubricants such as magnesium stearate or stearic acid, or talc; binders such as starch or sugars; fats, antioxidants, amino acids, proteins, nucleic acids, electrolytes, vitamins, derivatives thereof or combinations thereof. In one embodiment, an additive of the product is carob flour, for example, locust bean gum. In another embodiment, an additive is a mushroom extract from *Agaricus bisporus*. In particular embodiments, a product contains excipients such as magnesium stearate and/or stearic acid.

Further, to increase the palatability of a composition of this invention, it may be desirable to add flavors, sweetening agents, binders or bulking agents. Flavors which can optionally be added to the present compositions are those well-known in the art. Examples include, but are not limited to, synthetic flavor oils, and/or oils from plants leaves, flowers, fruits and so forth, and combinations thereof are useful. Examples of flavor oils include, but are not limited to, spearmint oil, peppermint oil, cinnamon oil, and oil of wintergreen (methylsalicylate). Also useful are artificial, natural or synthetic fruit flavors such as citrus oils including lemon, orange, grape, lime, and grapefruit, and fruit essences including apple, strawberry, cherry, pineapple and so forth. Sweetening agents can be selected from a wide range of materials such as water-soluble sweetening agents, water-soluble artificial sweeteners, and dipeptide-based sweeteners, including salts thereof and mixtures thereof, without limitation.

Binders can be selected from a wide range of materials such as hydroxypropylmethylcellulose, ethylcellulose, or other suitable cellulose derivatives, acrylic and methacrylic acid co-polymers, pharmaceutical glaze, gums (e.g., gum tragacanth), milk derivatives (e.g., whey), starches (e.g., corn starch) or gelatin, and derivatives, as well as other conventional binders well-known to persons skilled in the art. Examples of bulking substances include, but are not limited to, sugar, lactose, gelatin, starch, and silicon dioxide.

When the above-mentioned additives are included in the product of the present invention, they are generally less than 15% of the total product weight. In particular embodiments, they are less than 5 to 10% of the total product weight. The amount of each component of the present invention is in the range of 5% to 35% of the total weight of the instant composition. In certain embodiments, the xylooligosaccharide, arabinogalactan, *G. lucidum* beta glucan, insoluble yeast β (1, 3/1, 6)-glucan, and insoluble dried *S. cerevisiae* fermentate are each present in the range of 5% to 8% of the total weight of the instant composition; and the inulin and oat β (1, 3/1, 4)-glucan are each present the range of 25% to 32% of the total weight of the instant composition. The *B. coagulans* component of the instant composition can be present in the range 1.0 to 5.0 billion CFU or 2 to 10% of the total weight of the instant composition.

The composition of the present invention can be formulated as a tablet, capsule, sachet, powder, pill, soft gel, gelcap, liquid or as a food or beverage product such as solid food products like bars (e.g., nutritional bars or cereal bars), powdered drinks, dairy products, breakfast cereals, muesli, candies, confectioneries, cookies, biscuits, crackers, chocolate, chewing-gum, desserts and the like; or liquid comestibles, like soft drinks, juice, sports drinks, milk drinks, milk-shakes, yogurt drinks or soups, as well as pet treats, pet foods, etc.

The composition of the invention can optionally include conventional food additives, such as emulsifiers, stabilizers, sweeteners, flavorings, coloring agents, preservatives, chelating agents, osmotic agents, buffers or agents for pH adjustment, thickeners, texturizers and the like. In one embodiment, the composition includes a flavoring, e.g., an orange or citrus flavor.

Depending on whether the product is to be consumed by an adult human, child or animal (e.g., companion animal or livestock), it can be produced in various sizes and with various ingredients suitable for the intended recipient. Further, because the composition of the present invention is generally recognized as safe, they can be consumed one, two or three times daily or more. Repeated ingestion of the product of this invention will have a highly beneficial effect upon the intestinal microflora by localization and colonization in the large intestine of microbes known to promote a healthy intestinal microenvironment.

Preferably, a daily dose of the composition of the present invention would be one or two doses per day, wherein each dose contains between 2 and 4 grams of fiber. In certain embodiments, the composition is provided as a tablet containing 2 grams of fiber provided twice a day. In another embodiment, the composition is provided as a powder administered twice a day (4 grams of fiber per dose).

Given the activity of the instant composition, the present invention also relates to a method for improving or maintaining digestive health, weight and glucose balance. The method involves administering an effective amount of a product of the present invention composed of xylooligosaccharide, arabinogalactan, inulin, *Ganoderma lucidum* beta glucan, insoluble yeast β (1, 3/1, 6)-glucan, oat β (1, 3/1, 4)-glucan, and insoluble dried *S. cerevisiae* fermentate so that digestive health is improved or maintained, weight is maintained or reduced, and glucose levels are maintained or reduced desirably to a normal range. For example, a subject with a normal, healthy weight has a body mass index (BMI) in the range of 18.5 to 24.9, whereas overweight subjects have a BMI in the range of 25 to 29.9 and obese subjects have a BMI of 30 or more. Further, a normal sugar level is considered to be less than 100 mg/dL when fasting and less than 140 mg/dL two hours after eating. But in most healthy people, sugar levels are even lower. Administration of the composition of this invention will maintain a normal BMI or reduce BMI to the normal range and/or maintain or reduce sugar levels to a normal range.

Desirably, an effective amount of a composition of this invention is an amount sufficient to effect beneficial or desired results, including clinical results. As such, an effective amount of a composition of the invention is one which results in the alleviation or amelioration of one or more symptoms of diseases including autoimmune diseases, colon cancers, gastric ulcers, cardiovascular disease, chronic kidney disease, functional bowel diseases and obesity, which are mediated by intestinal microbiota. Administration of the instant composition can also diminish the extent of disease, stabilize (i.e., not worsening) the state of disease by supporting healthy bowel function, delay or slow disease progression, or amelioration or palliation of the disease state. Amelioration can also mean prolonging survival as compared to expected survival if not receiving treatment. In particular embodiments, the instant composition is administered to an obese subject. It is further contemplated that compositions of the present invention containing may have further utility in providing energy and overall health and well-being in subjects undergoing cancer therapy.

The amount and dosage regimen of the composition of the invention to be administered is determined in the light of various relevant factors including the purpose of administration (e.g., prevention, mitigation or treatment), the age, sex and body weight of an individual subject, and/or the severity of the subject's symptoms. In this respect, the compositions of the invention can be administered under the supervision of a medical specialist or may be self-administered.

The following non-limiting examples are provided to further illustrate the present invention.

Example 1: Enhanced Microbial Growth with a Multifiber Composition (KIBOW FORTIS®)

The multifiber product of the instant invention, with 7 different ingredients, was tested for its overall growth promoting activities on *L. acidophilus* and *B. longum*. The seven ingredient product of the instant invention known as KIBOW FORTIS® supported the growth of both beneficial species in vitro (FIG. 1).

Figure 2:
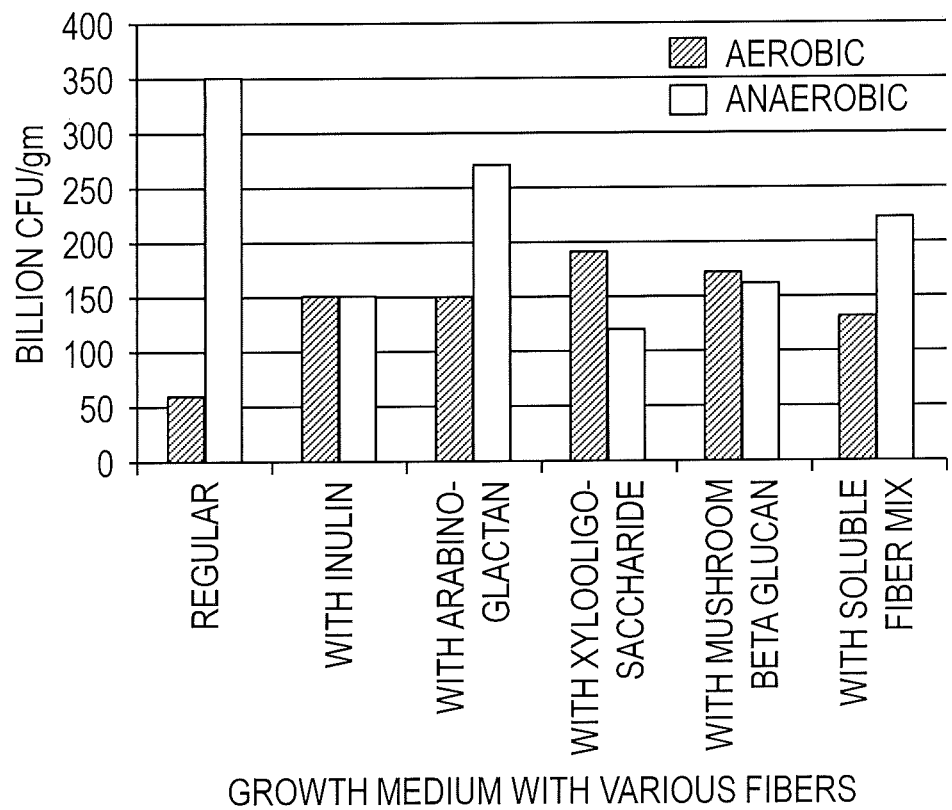
FIG. 2 depicts the effect of the multifiber formulation of the present invention on in vitro growth of *Bacillus coagulans*, under either aerobic or anaerobic growth conditions.

To test whether the multifiber formulation of the present invention can support the growth of another beneficial microbe, *B. coagulans*, experiments were conducted where *B. coagulans* growth in vitro was examined in the presence of soluble fibers individually, as well as the 7 ingredient multifiber product of the instant invention (KIBOW FORTIS®). Strains of *B. coagulans* were evaluated under both aerobic and anaerobic conditions. Results showed that *B. coagulans* was able to grow well in the presence of all of the individual fibers, as well as in the presence of the 7 multifiber product of the instant invention, both in the presence and absence of oxygen (FIG. 2).

Example 2: Comparison of the 7 Ingredient Multifiber Product (KIBOW FORTIS®) to Commercial Products The multifiber product KIBOW FORTIS® is desirably consumed once or twice daily, as a powder (see Sample 1, Table 1) or tablets (see Sample 2, Table 1), wherein each dose contains between 2 and 4 grams of fiber. Therefore, the product offers significant advantages over commercially available fiber supplements (Table 1) as it contains both soluble and insoluble fibers and provides between at least 4 grams of fiber per day.

TABLE 1

| Brand Name | Ingredient(s) | Serving size | Fiber content (gms) | Dosage per day |
| --- | --- | --- | --- | --- |
| METAMUCIL ® (dietary supplement) | Psyllium | 1 teaspoon | 3 | 3 |
| BENEFIBER ® (dietary fiber supplement) | Wheat Dextrin | 2 teaspoon | 3 | 3 |
| KONSYL | Psyllium | 1 teaspoon | 6 | 1 to 3 |
| CITRUCEL ® (Laxative) | Methyl Cellulose | 1 scoop | 2 | up to 3 |
| FIBERCHOICE | Inulin | 2 tablets | 3 | 3 |
| FIBERSURE | Inulin | 1 teaspoon | 5 | 3 |
| VITAFUSION FIBER WELL gummies | Polydextrose | 2 gummies | 5 | 1 |
| Sample 1 Powder | Multi-Inulin, Arabinogalactan, Xylooligosaccharide, Oat beta glucan, Mushroom beta glucan, Yeast beta glucan, Yeast fermentate | 1 scoop | 4 | 1 to 2 |
| Sample 2 Tablets | Multi-Inulin, Arabinogalactan, Xylooligosaccharide, Oat beta glucan, Mushroom beta glucan, Yeast beta glucan, Yeast fermentate | 3 tablets | 4 | 1 to 2 |

The prebiotic activity of KIBOW FORTIS® was compared with that of other known dietary fiber products (BENEFIBER® (dietary fiber supplement; Novartis AG), CITRUCEL® (Laxative; Merrell Dow Pharmaceuticals, Inc.) dietary fiber available from Glaxo Smith Kline and METAMUCIL® (dietary supplement; Proctor & Gamble Co.). BENEFIBER® (dietary fiber supplement; Novartis AG), a product intended for general gut health, is an oligosaccharide derived from wheat dextrin, which is easily hydrolyzed to sugar. METAMUCIL® (dietary supplement; Proctor & Gamble Co.) has *psyllium* husk, which provides satiety and reduces caloric intake, and has added sugar and flavor to appeal to the general customer; CITRUCEL® (Laxative; Merrell Dow Pharmaceuticals, Inc.) dietary fiber available from Glaxo Smith Kline contains methylcellulose, a bulk forming fiber laxative. Therefore, KIBOW FORTIS was compared with BENEFIBER® (dietary fiber supplement; Novartis AG), CITRUCEL® (Laxative; Merrell Dow Pharmaceuticals, Inc.) and METAMUCIL® (dietary supplement; Proctor & Gamble Co.). The probiotic bacteria *L. acidophilus* and *B. longum* were grown on solid agar medium containing these multi fibers as the sole source of "carbon" for growth in place of sugar which is the normal source.

The Bifidobacteria counts were similar across products; however, the abundance of growth as seen by the colony size indicated BENEFIBER® (dietary fiber supplement; Novartis AG) to be least supportive for growth of bifidobacteria. METAMUCIL® (dietary supplement; Proctor & Gamble Co.) and CITRUCEL® (Laxative; Merrell Dow Pharmaceuticals, Inc.) dietary fiber available from Glaxo Smith Kline showed smaller colonies due to the presence of the added sugar in the product. Sugars are easily assimilable by all bacteria, more so by the pathogenic organisms. Fibers however are only fermented or metabolized by the probiotic bacteria like the lactobacilli and bifidobacteria. Highest growth was seen with the KIBOW FORTIS® product, which is a 7 ingredient multi-fiber product whose 7 multi-fiber ingredients are also found within the composition of the present invention.

Example 3: Amelioration of Obesity and Enhancing Potential Weight Loss

Obesity is now an epidemic in the developed world driven by consumption of high calorie processed foods and a sedentary lifestyle. It is a universal problem and many groups are working towards understanding the causes and on reducing this epidemic. A large number of probiotic formulations are available on the market for digestive health. Probiotic bacteria which are predominantly the Lactobacilli and Bifidobacteria need to be consumed in large amounts for them to be effective. Studies have categorized the human gut microbiota into three distinct groups/clusters or enterotypes, which are enriched in *Bacteroides, Prevotella* or *Ruminococcus* (Arumugam, et al. (2011) *Nature* 473:174-180). Type 1 is enriched in Bacticides and derives energy form carbohydrates and proteins; enterotype 2 is enriched in *Prevotella* which are mucin degraders and enterotype 3 is predominantly *Ruminococcus*, which degrade mucin and sugars for energy. Obesity models in mice (ob/ob mice) have been shown to have 50% fewer Bacteroidetes and a proportional increase in Firmicutes, suggesting that the nature of the gut microbiota has a very important role to play in obesity (Ley, et al. (2005) *Proc. Natl. Acad. Sci. USA* 102:11070-5). Further, in obese and overweight children, it was shown that there is a lack of beneficial bacteria and an increase in *Staphylococcus aureus*, a Firmicute (Kalliomaki, et al. (2008) *Am. J. Clin. Nutr.* 87:534-538). Moreover, recent studies have revealed that inflammation has a major role in obesity. Data now provide evidence that this inflammation is caused by gut bacteria and that these bacteria also influence development of obesity (Cani & Delzenne (2009) *Curr. Pharm. Des.* 15:1546-58; Ley (2010) *Curr. Opin. Gastroenterol.* 26:5-11; Vrieze, et al. (2010) *Diabetologia* 53:606-13).

Probiotics have been used in various clinical trials for obesity in mice and rats. Most of the studies in rats were carried out using single strain of the probiotic bacteria at maximum dose of 10 billion CFU/day and a reduction in body weight and adipocyte size was seen. Sprague-Dawley rats have also exhibited a decrease in leptin when *L. plantarum* was fed. Moreover, *S. boulardii* administration results in a decrease in low grade systemic and hepatic inflammatory markers such as interleukin-1β, IL-6, IL-4 and TNF-α. However, for probiotics to be effective, they have to be consumed in large numbers (billions) to compete with the native microbes of the gut, which are in the trillions.

Alternatively, gut microflora growth can be enhanced using prebiotics. However, prebiotics obtained from ingestion of food are typically excreted out of the body undigested. In addition, to obtain an effective amount of prebiotic from food, large amounts of food would need to be consumed (25 to 35 grams) each day.

It has now been shown that replacing the sugar of bacterial growth medium with pure fibers leads to an enhanced growth of lactobacilli and bifidobacteria in hundreds of billions. This indicates that gut microflora can be restored by consuming these pure dietary fibers in a consumer product (e.g., micronized or powder formats). The selected prebiotic dietary fibers, both soluble and insoluble, have other beneficial properties as well including immunostimulatory, satiety, cholesterol reduction, and the ability to promote much greater growth of beneficial lactobacilli and bifidobacteria. Data revealed that the counts of lactobacilli and bifidobacteria increased over 300 billion each with just one gram of the fiber in the growth medium. The results indicated that there is a logarithmic increase in the growth of the probiotic bacterial species with prebiotics as the carbon source. Human consumption of 4 to 8 g/day of pure micronized or powder form of fibers is expected to provide between 2.4 trillion to 4.8 trillion beneficial microbes, thereby having a great potential to offset the dysbiosis related to obesity.

To analyze the effect of the instant composition in treating obesity, obese-prone rats (OP-CD) are employed. Developed from a line of Crl:CD(SD) rats, OP-CD rats were obtained by selecting future breeders with accelerated weight gain. Two lines are developed from this outbred colony, the OP-CD (Obese Prone) and OR-CD (Obese Resistant). The OP-CD becomes obese when fed high-fat diets eliminating the subpopulation of non-responders. Polygenic obesity develops despite having a fully functioning leptin receptor. By comparison, the OR-CD rat does not become obese (non-responder) when fed high-fat diets.

Rats (n=6) are fed ad libitum a formulation of soluble and insoluble multifiber prebiotics (10% w/w) and *B. coagulans* in standard rat chow. Control rats (n=6) are fed normal rat chow devoid of the multi-fiber/*B. coagulans* formulation. Weight, BMI, blood pressure, and hematological (CBC) and basic metabolic markers (CRP, cholesterol and triglycerides profile) are measured at baseline, 4-, 8- and 12-week periods. Secondary end points include biochemical parameters (Leptin, Ghrelin and Fetuin), urine collection, and fecal analysis. Inflammatory biomarkers, such as NF-κB TNF-α, IL-6 are also tested.

It is expected that the multifiber prebiotic composition of the invention will modulate the gut microbiome of rats thereby ameliorating or treating obesity in obese-prone rats.

Example 4: Health Bar

Health bars can be prepared by combining various excipients, such as binders, additives, flavorings, colorants and the like, along with the prebiotic fibers of this invention (i.e., xylooligosaccharide, arabinogalactan, inulin, *Ganoderma lucidum* beta glucan, insoluble yeast β(1,3/1,6)-glucan, soluble oat β(1,3/1,4)-glucan, and insoluble dried *Saccharomyces cerevisiae* fermentate), and mixing to a plastic mass consistency. The mass is then either extruded or molded to form "candy bar" shapes that are then dried or allowed to solidify to form the final product.

Example 5: Medical Food

A medical food can be prepared by combining rolled oats, dehydrated apples, honey, carob flour, cinnamon, sugar, vanilla extract, and prebiotic fibers (i.e., xylooligosaccharide, arabinogalactan, inulin, *Ganoderma lucidum* beta glucan, insoluble yeast β(1,3/1,6)-glucan, soluble oat β(1,3/1, 4)-glucan, and insoluble dried *Saccharomyces cerevisiae* fermentate). These ingredients are mixed in appropriate proportions and formed into a rectangular bar approximately 12.5 to 15 centimeters in length, 3 to 4 centimeters in width and 1 centimeter in height and placed into a sterile vacuum oven for 12 to 24 hours to obtain an edible food product of the desired consistency.

Example 6: Quorum Sensing Inhibition (QSI)

It has been shown that many lactobacilli produce antimicrobial compounds that can interfere with virulence or pathogenic properties of enteric pathogens such as *Pseudomonas aeruginosa*, *Escherichia coli*, *Salmonella typhi*, *Shigella* etc. (Servin (2004) *FEMS Microbiol. Rev.* 28:405-440; Varma, et al. (2010) *J. Food Sci.* 75:M546-M551). Thus, one strategy for virulence attenuation is based upon the production of certain metabolites produced by probiotic strains. For example, soluble molecules have been found to accumulate in the supernatant of *Lactobacillus paracasei* subsp *paracasei* CMGB 18, which have inhibitory properties on multidrug resistant *P. aeruginosa* and on quorum sensing (QS) gene expression (Cotar, et al. (2010) *Roum Arch. Microbiol. Immunol.* 69:213-223; Cotar, et al. (2013) *Curr. Organic Chem.* 17:155-161). Such compounds have been termed quorum sensing inhibitors (QSI).

*Staphylococcus aureus* produces exotoxins, which lead to the menstrual-associated toxic shock syndrome. In culture, human vaginal isolate *L. reuterii* RC-14 produces cyclic dipeptides cyclo(L-Phe-L-Pro) and cyclo(L-Tyr-L-Pro), which have been suggested to interfere with the staphylococcal quorum-sensing system agr, a key regulator of virulence genes, and repress the expression of toxin in *S. aureus* MN8 (Li, et al. (2011) *Proc. Natl. Acad. Sci. USA* 108:3360-3365).

Prebiotics promote the growth of probiotic lactobacteria and bifidobacteria. Given that the instant composition has prebiotic properties, it is of use in increasing the growth of the beneficial bacteria and native probiotic strains. Increased growth of these beneficial microbes to the level of trillions leads to the production of metabolites that can act as QSI thereby preventing growth of virulent pathogenic bacteria and reducing infection and inflammation. Increased growth of these beneficial microbes will also lead to decreased production of toxic metabolites. As such, gut dysbiosis is corrected and a balanced gut microbiome restores health to the human subject.

Example 7: Efficacy of Multi-Fiber Formulation with and without B. coagulans In Vitro An experiment was performed to compare two fiber mixtures in a long-term administration study using a continuous model of the human gastrointestinal tract known as the Simulator of the Human Intestinal Microbial Ecosystem (SHIME®; Molly, et al. (1994) *Microbial Ecol. Health Dis.* 7:191-200; Ranganathan, et al. (2006) *ASAIO J.* 52:70-79). This model allows for culture of the complex gut microbiota over a longer period under representative conditions of the different intestinal regions. Therefore, the SHIME model allows for collection of detailed information about the fermentation profile of probiotic and/or prebiotic formula, as well as collecting information on the localization of the intestinal fermentation activity that is affected by treatments. The experiments were run to compare, side-by-side, and the activity of the instant multi-fiber prebiotic formulations both with addition of B. coagulans and without the addition of B. coagulans (KIBOW FORTIS®).

Each unit of the SHIME® used consisted of an ascending, transverse and descending colon region. Briefly, during a two-week control period, baseline values for microbial activity (e.g., SCFA, lactate, ammonium) and microbial composition were established. After the control period, a three-week treatment period was initiated, during which each of the products was supplemented to the control diet. Each segment of the SHIME® consisted of a succession of 4 reactors simulating the different parts of the gastrointestinal tract (i.e., stomach and small intestine; ascending colon; transverse colon; descending colon). The colonic reactor compartments were continuously stirred reactors with constant volume and pH control. Two vessels were used to simulate the stomach and small intestine, and five colon vessels were used to assess the effect of the two multi-fiber compositions. In the colon vessels, each unit consisted of an ascending (pH 5.6-5.9; volume 500 ml), transverse (pH 6.15-6.4; volume 800 ml) and descending (pH 6.6-6.9; volume 600 ml) colon compartment. The experiments consisted of three stages: 1) stabilization period; 2) control period; and 3) treatment period. During the stabilization period, after inoculation of the colon reactors with a fresh fecal sample, a two-week stabilization period allows the microbial community to differentiate in the different reactors depending on the local environmental conditions. During this period the basic nutritional matrix was provided to support the maximum diversity of the gut microbiota originally present in the fecal inoculum. During the control period (2-week reference period), the standard SHIME nutrient matrix was further dosed to the model for a period of 14 days. Analysis of samples in this period allowed for determination of baseline microbial community composition and activity in the different reactors, which will be used as a reference for comparison to results from the multi-fiber treatments. During the treatment period (3 weeks), the SHIME® reactor was operated under nominal conditions, but with a diet supplemented with the multi-fiber prebiotic products on top of the normal composition.

Effects During the Stabilization Period. During the stabilization period, the activity monitored included pH decreases and total gas production (indicative of fermentation activity). During the control and treatment portions of the SHIME® experiments, the endpoints monitored included acid/base consumption as well as microbial community activity (twice each week), microbial community composition (once each week), and gut barrier activity.

For acid/base consumption, the production of microbial metabolites in the colon reactors is known to alter pH. Without continuous pH control (through the addition of acid or base), the pH would exceed the fixed intervals. Therefore, consumption of acid/base is continuously monitored during a SHIME® experiment. With respect to microbial community activity, both short-chain fatty acid (SCFA) concentrations, lactate levels, and levels of ammonium ions and branched SCFAs were measured. SCFAs monitored included the concentration of acetic acid, propionic acid and butyric acid. With respect to lactate, the human intestine harbors both lactate-producing and lactate-utilizing bacteria. Lactate is produced by lactic acid bacteria and decreases the pH of the environment acting also as an antimicrobial agent. It can also be rapidly converted into acetate, butyrate, and propionate by other microorganisms. Ammonium and branched SCFAs (isobutyric acid, isovaleric acid and isocaproic acid) are markers of proteolytic fermentation, and can have adverse effects on host health. With respect to the composition of the microbial communities that are found before, during and after exposure to the multi-fiber compositions of the instant invention, the following groups were quantified in the lumen via qPCR: 1) two main bacterial phyla of the human gut microbiome, i.e., Firmicutes and Bacteroidetes; 2) two beneficial probiotic bacteria, Bifidobacteria and lactobacilli; and 3) *Akkermansia muciniphila, Blautia coccoides* and *Eubacterium rectale*, and *Faecalibacterium prausnitzii*. With respect to modulation of gut-wall function, the effect of the compositions of the instant invention on the host was evaluated in terms of gut barrier activity (TEER and LY permeation), and production of pro-inflammatory and anti-inflammatory cytokines (i.e., NF-κB, TNF-α, IL8, IL6, and IL10).

Gas pressure significantly increased for both multi-fiber products relative to the control, indicating that both compositions were fermented by the colonic microbiota. Both prebiotic mixtures yielded a similar gas production at the end of the incubation period (48 hours) (i.e., 89.7 kPa for the composition with *B. coagulans;* 90.4 kPa for the composition without *B. coagulans*). Both products showed significant gas production after four hours of incubation, and measurements showed that the amount of gas production between six hours and 24 hours of incubation was similar. There was no significant gas production after 24 hours of incubation, likely due to depletion of the products.

Monitoring of the pH during colonic incubation provided a first indication of the production of SCFA and ammonium ions (NH4+). In general, a pH drop is observed during the first 24 hours of incubation, due to the formation of SOFA and lactate. This pH drop is often followed by a pH increase during the last 24 hours of incubation due to proteolytic fermentation, which results in the production of, amongst others, NH4+. A large pH drop was associated with fermentation of both products, relative to the control (decreased by at least 0.5 pH units), indicating that both multi-fiber compositions were fermented by the colonic microbiota. The pH drop was similar for both products and most pronounced during the first 24 hours of incubation, confirming the results obtained with the gas production measurements. During the second 24 hours of incubation, however, there was a slight pH increase, likely due to depletion of the fibers and the subsequent switch of the bacterial metabolism to proteolytic fermentation. These data show significant increases in gas production combined with a large pH decreases indicated that both products are readily fermented by the human gut microbiome, resulting in the formation of several potentially health-related metabolites such as SCFA and lactate.

Effects During the Control Period. During the control period, SCFA levels were very stable (on average 94.0% similar between consecutive time points in control period) and reproducible between each of the two SHIME units (on average 91.5% similar). This indicated that the microbial communities were stable in terms of activity and composition. This high stability was important in terms of data interpretation as it indicates that any effects observed during the treatment resulted from the administered multi-fiber compositions, while the high reproducibility between both units allowed for the direct comparison between the compositions.

The consumption of acid and base reflects the overall microbial activity throughout a SHIME® experiment. To make sure that optimal environmental conditions are maintained, the pH in a SHIME® system is controlled by pH controllers between 5.6-5.9 in the ascending colon, 6.15-6.4 in the transverse colon and 6.6-6.9 in the descending colon. Upon stabilization of the microbial community in the different reactors (starting from 2 weeks after inoculation), base-acid consumption is generally low. However, during a treatment, bacteria may produce increased amounts of SCFA. As a consequence, the environment in the reactors will acidify, requiring administration of base to the respective reactors to keep them in the pre-set pH-ranges. As a result, the acid/base consumption will increase. By measuring the acid/base consumption throughout an experiment, the potential fermentation of the multi-fiber products was estimated.

Both multi-fiber products were well fermented, as they were associated with increased base consumption immediately after administration of the treatment. Both compositions resulted in a similar level of acidification (and thus increased base consumption) in all three colon compartments, with an initially higher increase for the product without *B. coagulans* in the ascending colon. The observed acidification (compensated by base addition) was attributed to increased levels of SCFA and/or lactate in the vessels. Compared to the ascending and transverse colon, base consumption was relatively low for both products in the descending colon. Lower fermentation in the descending colon is believed to be related to the complete degradation of the fibers in the preceding ascending and transverse colon vessels.

Figure 3A:
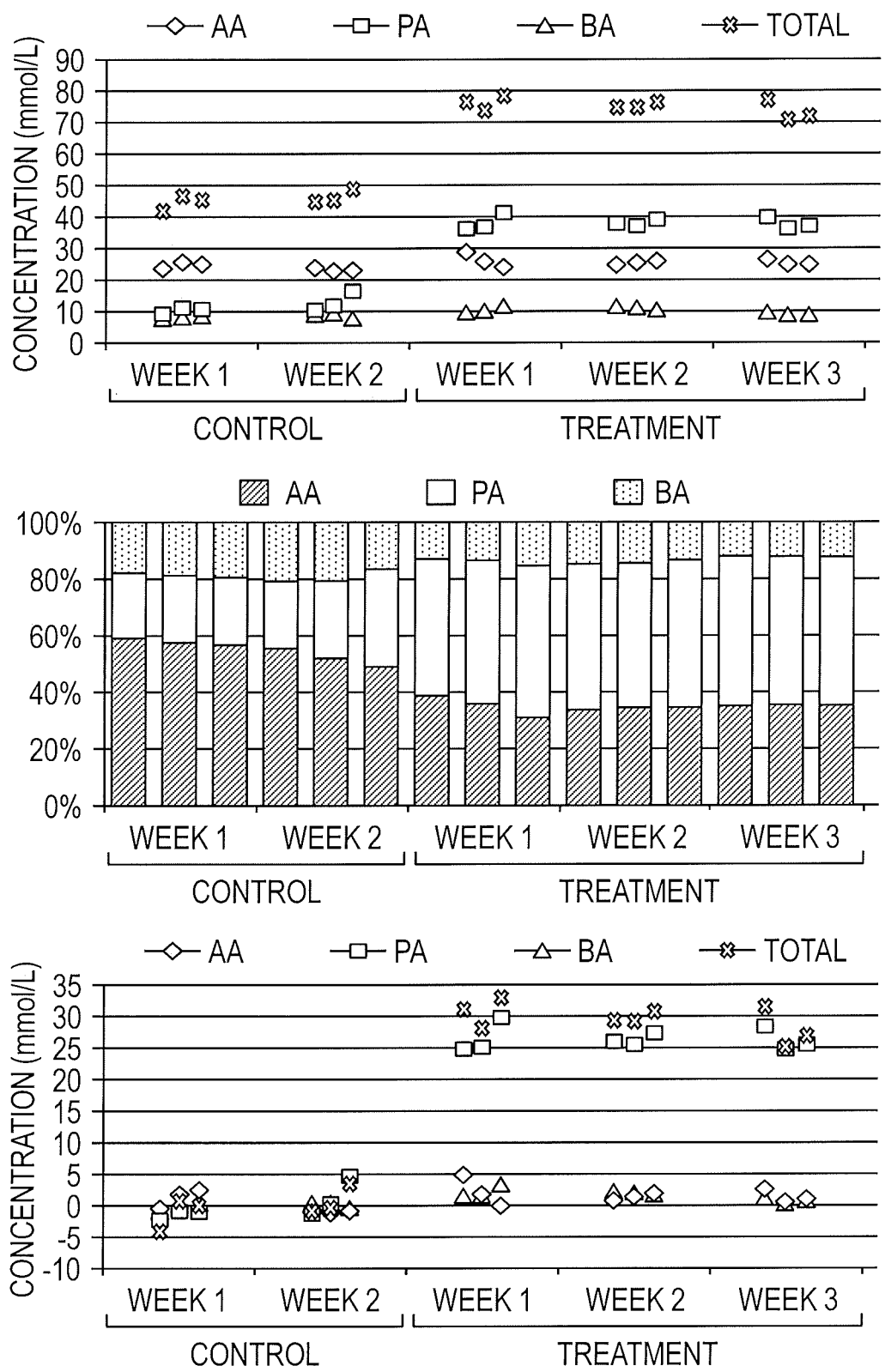
FIGS. 3A, 3B and 3C depict the absolute (upper panel), proportional (middle panel), and normalized (lower panel) values of acetic acid (AA), propionic acid (PA), butyric acid (BA), and total SCFA (total) in the ascending colon reactor (FIG. 3A), transverse colon (FIG. 3B) and descending colon (FIG. 3C) treated with the multi-fiber composition of the instant invention with *B. coagulans* as a component. Shown are the results of three samples taken during two control and three treatment weeks.
Figure 3B:
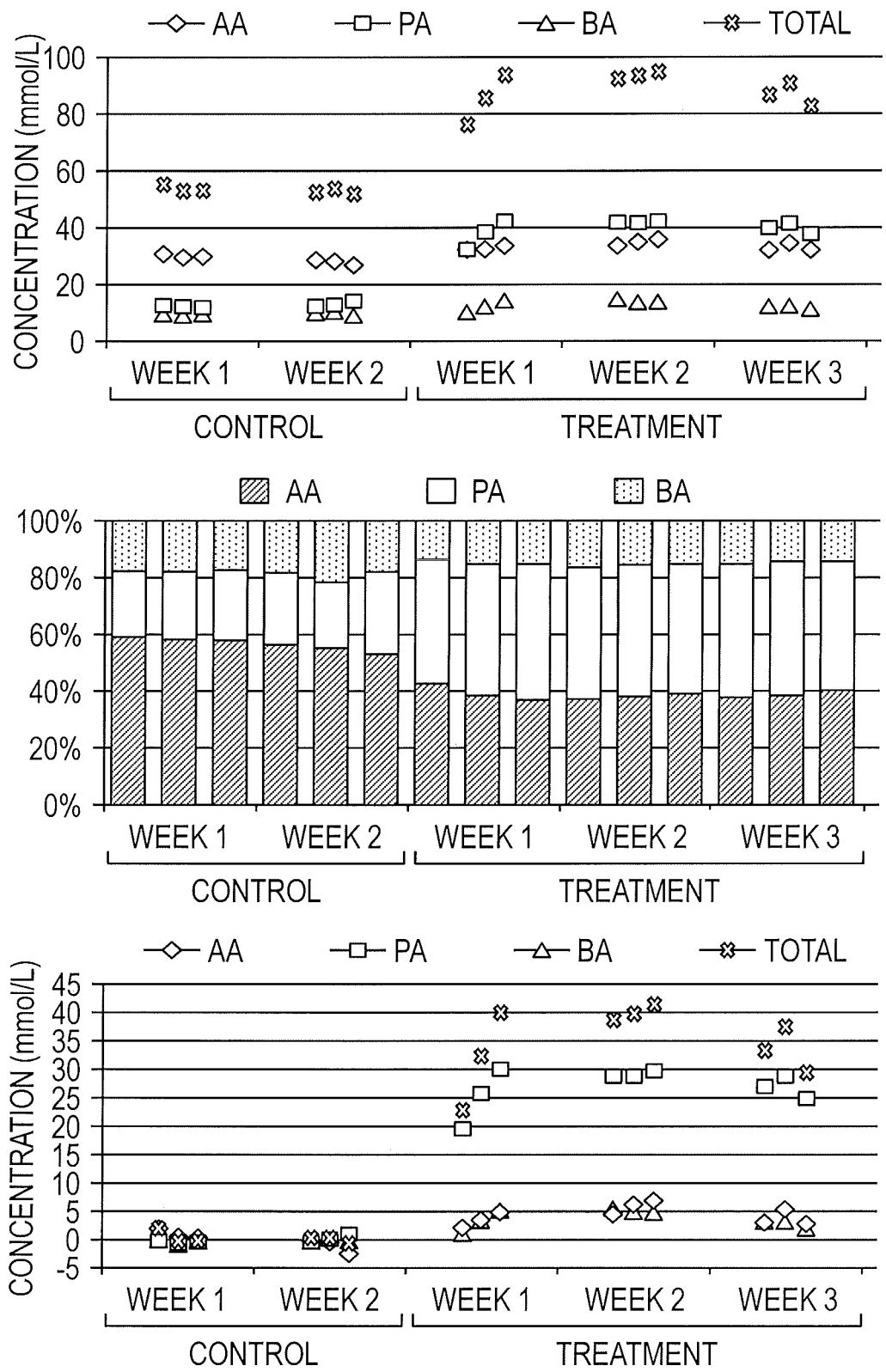
Figure 3C:
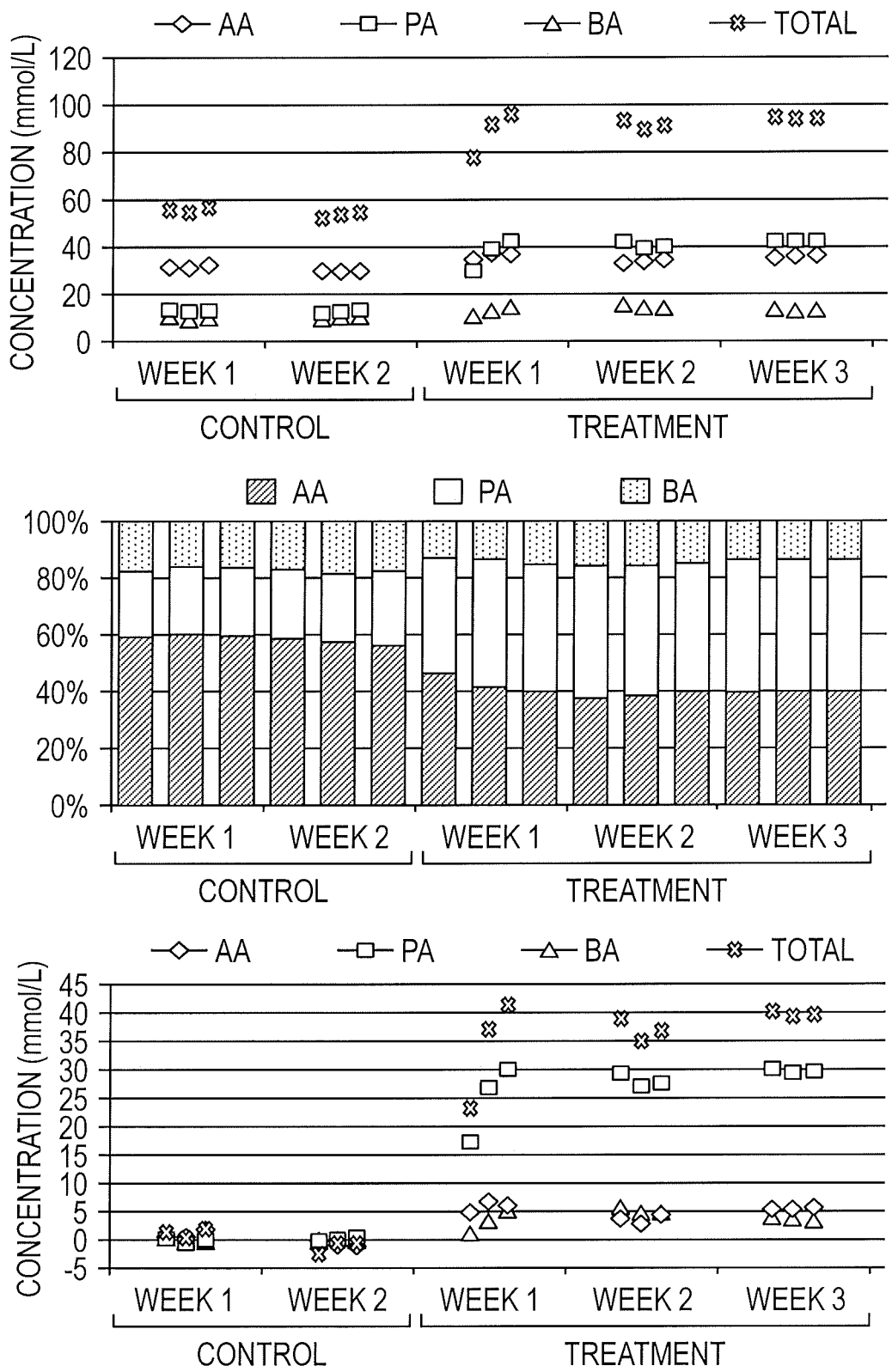
Figure 4:
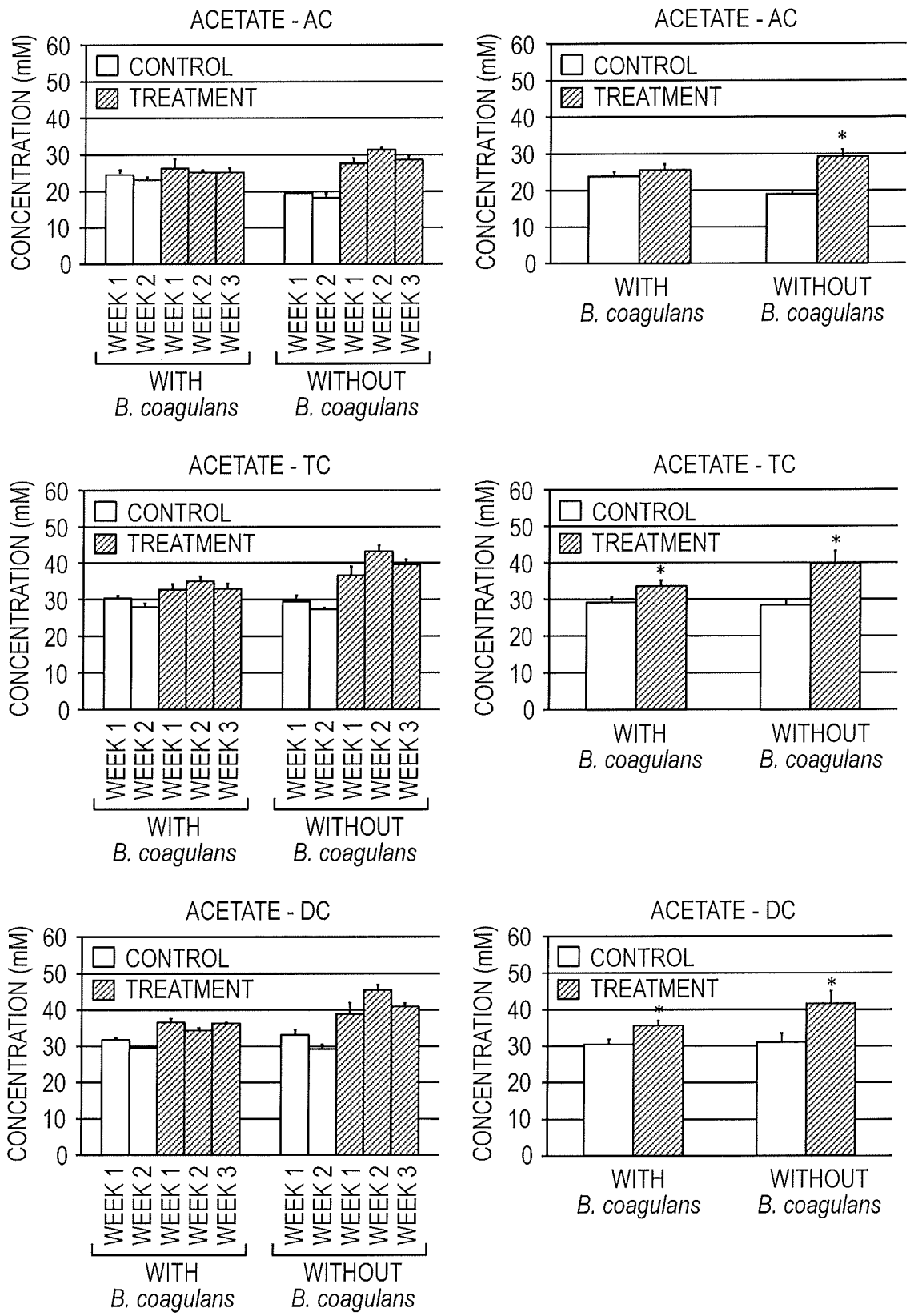
FIG. 4 depicts the effect of the multi-fiber compositions of the present invention on acetate production in the ascending (AC; upper), transverse colon (TC; middle), and descending colon (DC; lower). Left: average weekly acetate production during control or treatment weeks (n=3), right: average acetate production over the control (n=6) and treatment period (n=9) (* indicates statistically significant differences).
Figure 5:
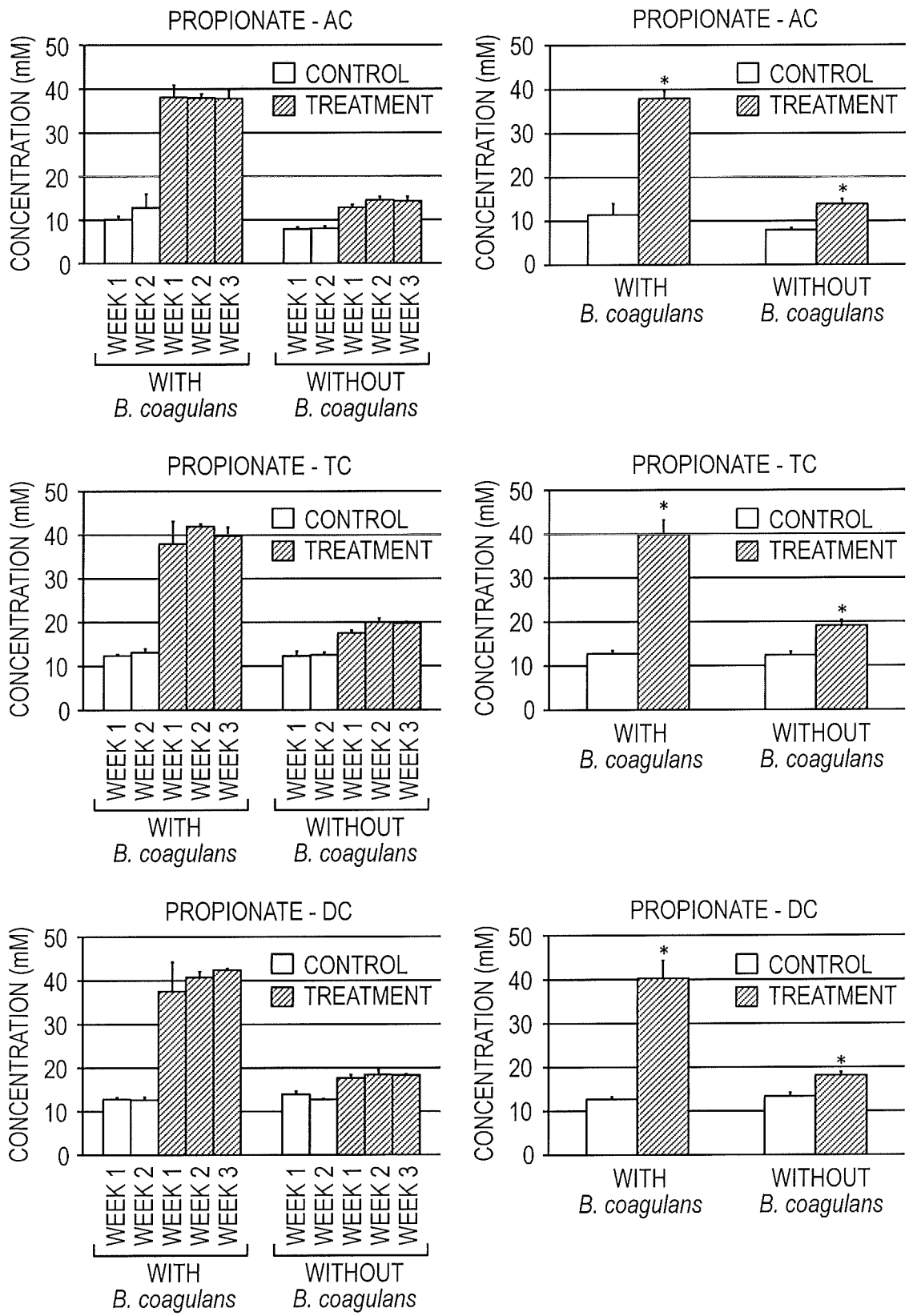
FIG. 5 depicts the effect of the multi-fiber compositions of the present invention on propionate production in the ascending (AC; upper), transverse colon (TC; middle), and descending colon (DC; lower). Left: average weekly propionate production during control or treatment weeks (n=3), right: average propionate production over the control (n=6) and treatment period (n=9) (* indicates statistically significant differences).
Figure 6:
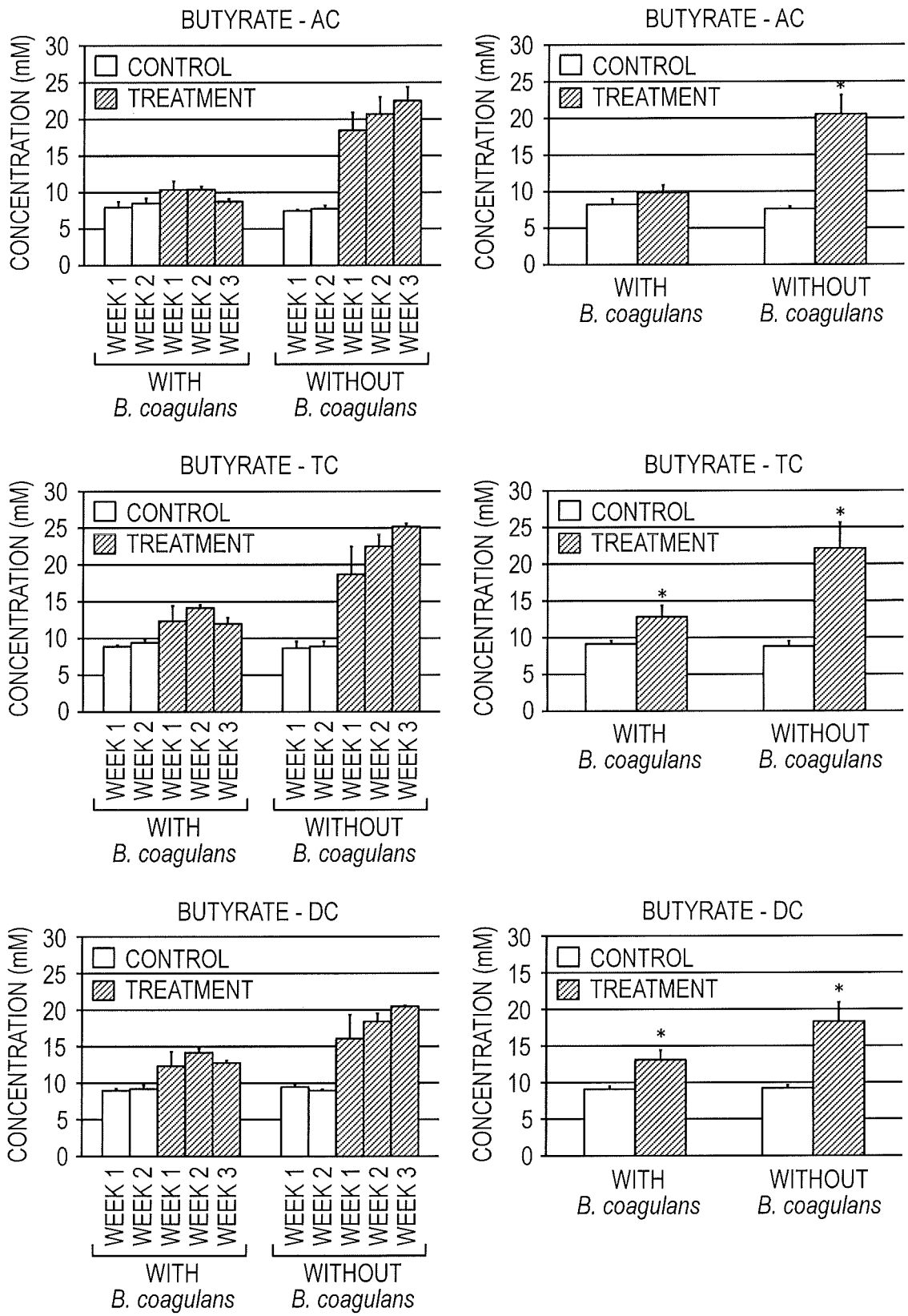
FIG. 6 depicts the effect of the multi-fiber compositions of the present invention on butyrate production in the ascending (AC; upper), transverse colon (TC; middle), and descending colon (DC; lower). Left: average weekly butyrate production during control or treatment weeks (n=3), right: average butyrate production over the control (n=6) and treatment period (n=9) (* indicates statistically significant differences).
Figure 7A:
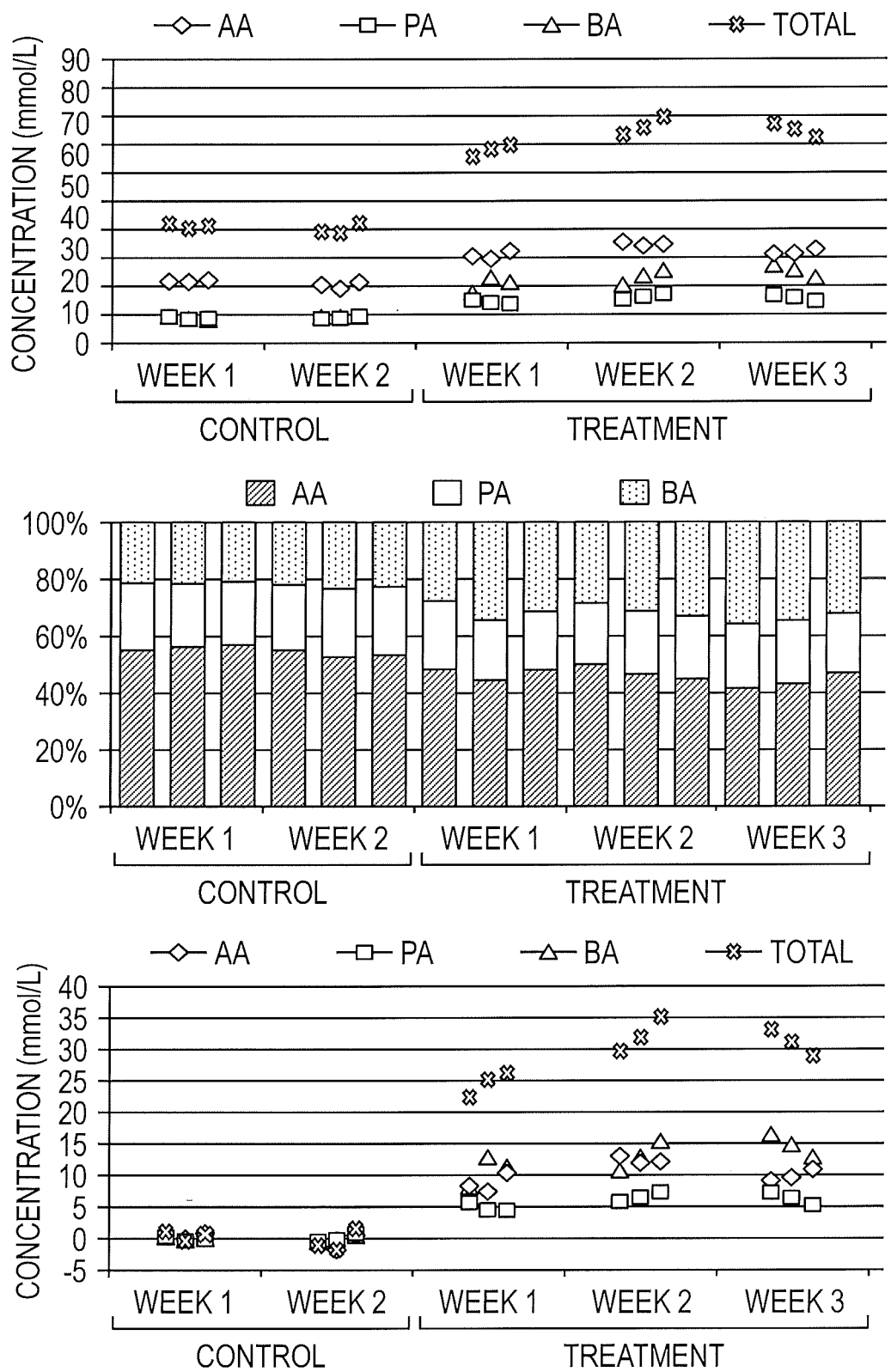
FIGS. 7A, 7B and 7C depict the absolute, proportional, and normalized values of acetic acid (AA), propionic acid (PA), butyric acid (BA), and total SCFA (total) in the ascending colon reactor (FIG. 7A), transverse colon (FIG. 7B) and descending colon (FIG. 7C) treated with the multi-fiber composition of the instant invention without addition of *B. coagulans* as a component. Shown are the results of three samples taken during two control and three treatment weeks.
Figure 7B:
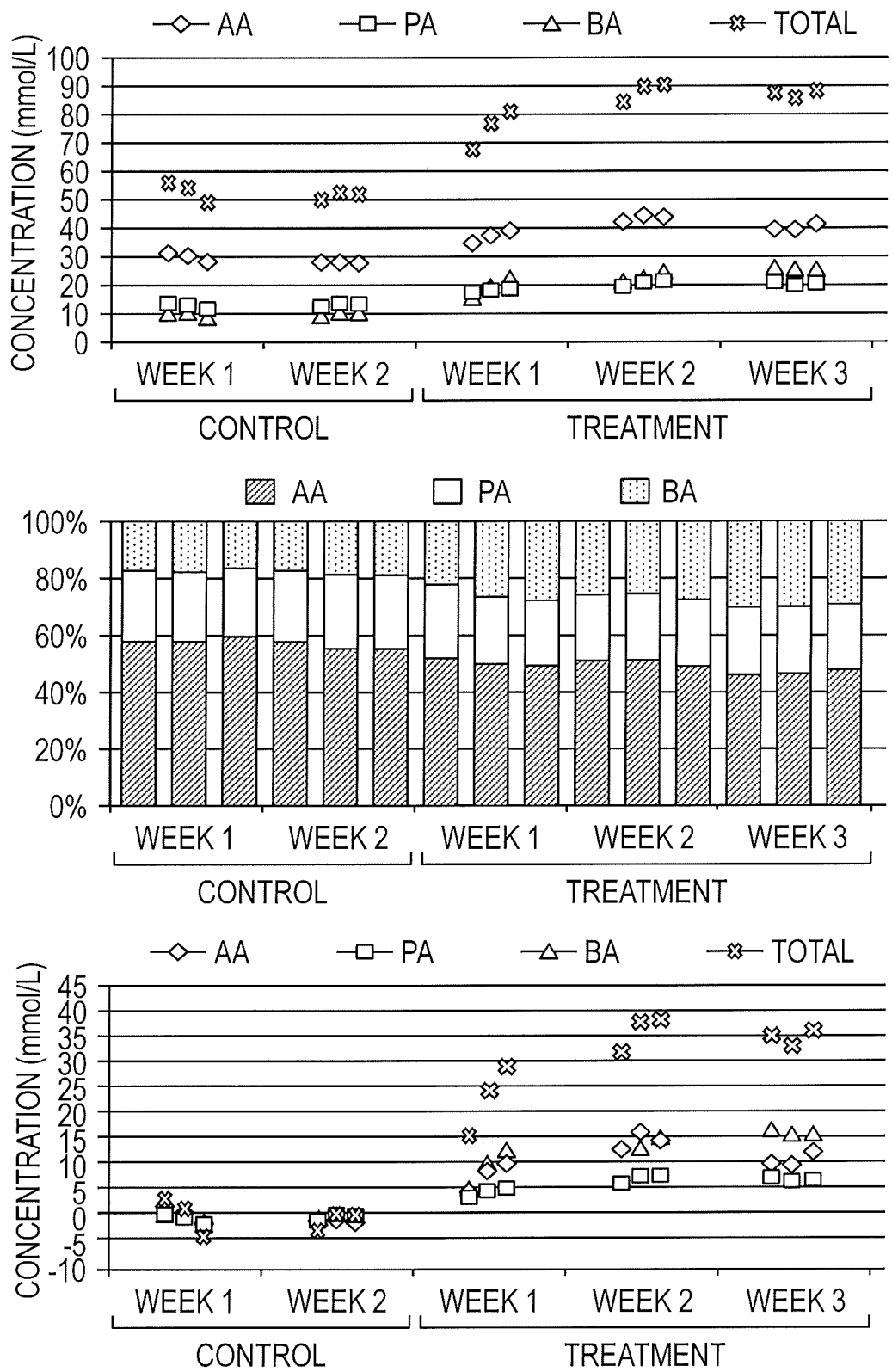
Figure 7C:
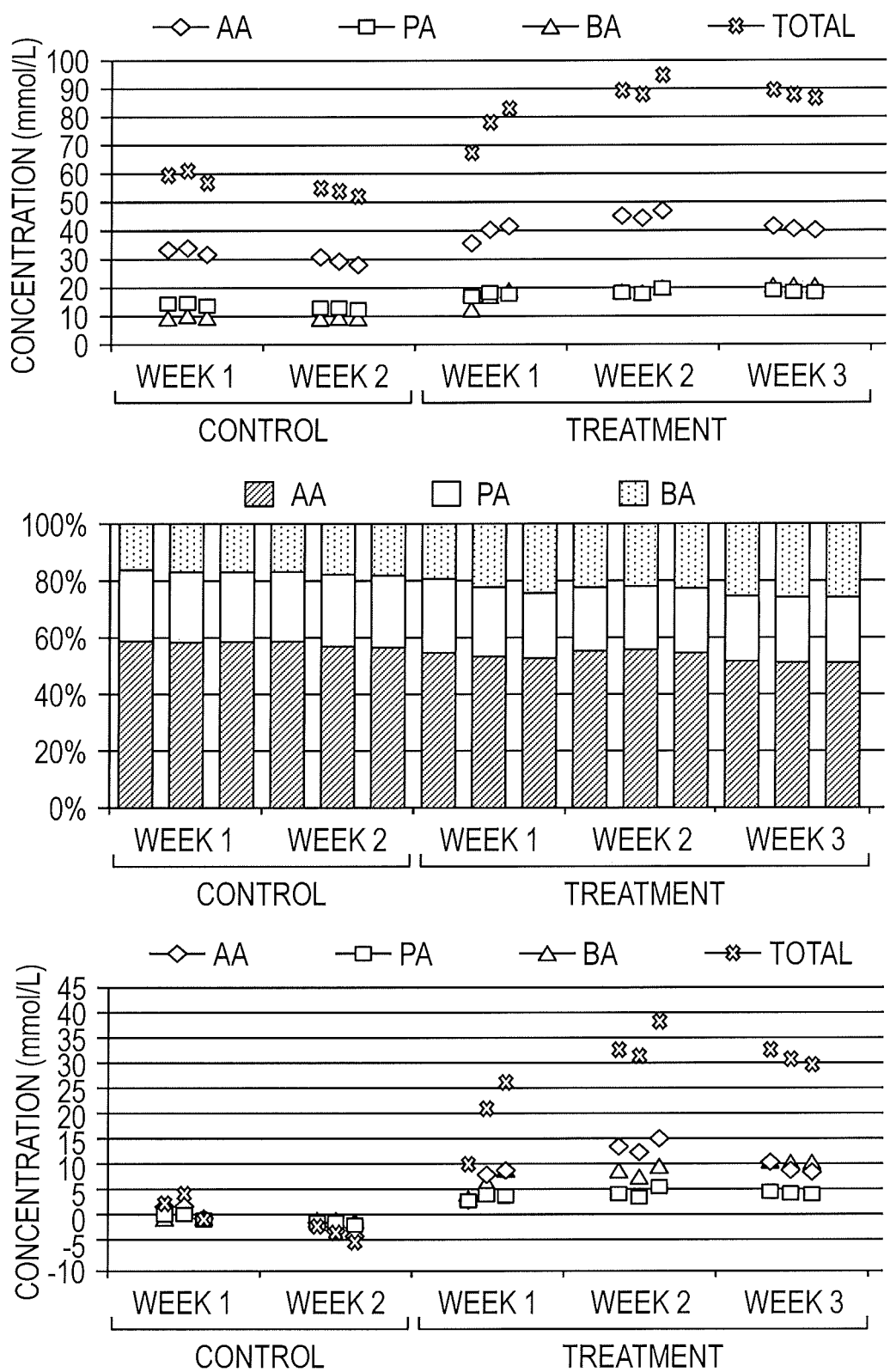

Effects During Treatment with Multi-Fiber Compositions. Next, the effects of the multi-fiber compositions with and without *B. coagulans* on SCFA production in the SHIME® were investigated. SCFA production results to carbohydrate metabolism in the colon and is related with various health effects. The most abundant SCFAs are acetate, propionate and butyrate. SCFAs are well-known to play a crucial role in gut health. Acetate can be used as an energy source for the host and as a potential substrate for lipid synthesis in the body. Moreover, it is an important byproduct in the synthesis of butyrate. The health-promoting effects of SCFAs, however, are mainly attributed to propionate and butyrate, which act as the main energy sources for the gut epithelium (Cummings & Englyst (1987) *Am. J. Clin. Nutr.* 45:1243-1255) and have shown protective effects against inflammation and colon cancer. Propionate is known to be transported to the liver, where it has a cholesterol-lowering effect in plasma (Wright, et al. (1990) *Exp. Biol. Med.* 195:26-29; Demigne, et al. (1995) *Br. J. Nutr.* 74:209-219) and positively affects glycemic control (Wong, et al. (2006) *J. Clin. Gastroenterology* 40:235-243). Results of the experiments where colon was treated with multi-fiber compositions with *B. coagulans* as a component are shown in FIGS. 3A, 3B and 3C as well as FIGS. 4-6. Treatment with the multi-fiber composition containing *B. coagulans* was associated with 1) an immediate increase in total SCFA production, mainly due to an increased production of propionate over all three colon regions tested; 2) no increase in acetate and butyrate levels in the ascending colon vessel, and minor increases in acetate and butyrate levels in transverse and descending colon vessels; 3) a shift in SCFA levels from an acetate-dominant to a propionate-dominant profile; 4) constant levels in both absolute and proportional SCFA levels during the entire treatment period in the ascending colon; and 5) stabilization of absolute and proportional SCFA levels at the last sampling point of week one for the transverse and descending colon vessels. Considering the immediate response to product supplementation in the ascending colon, a large proportion of the multi-fiber compositions are likely converted in the ascending colon, resulting in production of propionate. Therefore, only small doses of the multi-fiber compositions likely reach the transverse and descending colon with every feeding cycle. In these distal regions, the gradual increase in propionate (and hence total SCFA) levels relative to the ascending colon was attributed to the wash-out of these SCFA from the ascending colon, while small additional quantities of acetate, propionate and butyrate were produced.

Results of the experiments where treatment was with the multi-fiber composition without *B. coagulans* are shown in FIGS. 7A, 7B and 7C and FIGS. 4-6. SHIME® treatment with the multi-fiber composition without *B. coagulans* added was associated with 1) an immediate increase in total SCFA production, mainly due to an increased production of acetate and butyrate, and to a lesser extent also propionate, over all three colon regions tested; 2) production of butyrate at the expense of acetate (proportional production levels); and 3) constant absolute and proportional SCFA levels during the entire treatment period in the ascending colon, becoming stable on the last sampling point of week one in the transverse and descending colon vessels. Similar to the results observed with SHIME treatment with the multi-fiber compositions with *B. coagulans*, a more gradual increase in SCFA levels relative to the ascending colon was observed in the transverse and descending colon, most likely due to the wash-out effect from the ascending colon. Considering the immediate response to product supplementation in the ascending colon, a large proportion of the multi-fiber composition was likely converted in the ascending colon, again resulting in lower doses reaching the transverse colon.

The human intestine harbors both lactate-producing and lactate-utilizing bacteria. Lactate is produced by lactic acid bacteria and decreases the pH of the environment. Especially at low pH values, lactate can exert strong antimicrobial effects against pathogens. Another beneficial effect of lactate results from its conversion to butyrate by specific lactate-utilizing butyrate-producing microorganisms such as *Anaerostipes caccae, Anaerostipes hadrus* or *Eubacterium hallii*. As different microbial species produce and convert lactate, an increase of lactate concentration can result from an increased production, as well as a decreased conversion.

During the control period (discussed supra), lactate levels were higher in all colonic compartments for both products as compared to levels achieved during the treatment period. Yet, the difference was statistically significant only when the results of treatment with the multi-fiber composition without B. coagulans were compared to the control period across all vessels. Considering that lactate can be converted into butyrate through cross-feeding, and since butyrate levels increased upon treatment with this composition without B. coagulans, the decrease in lactate concentrations likely was attributable to a more efficient conversion into butyrate with the addition of B. coagulans to the mixture.

Figure 8:
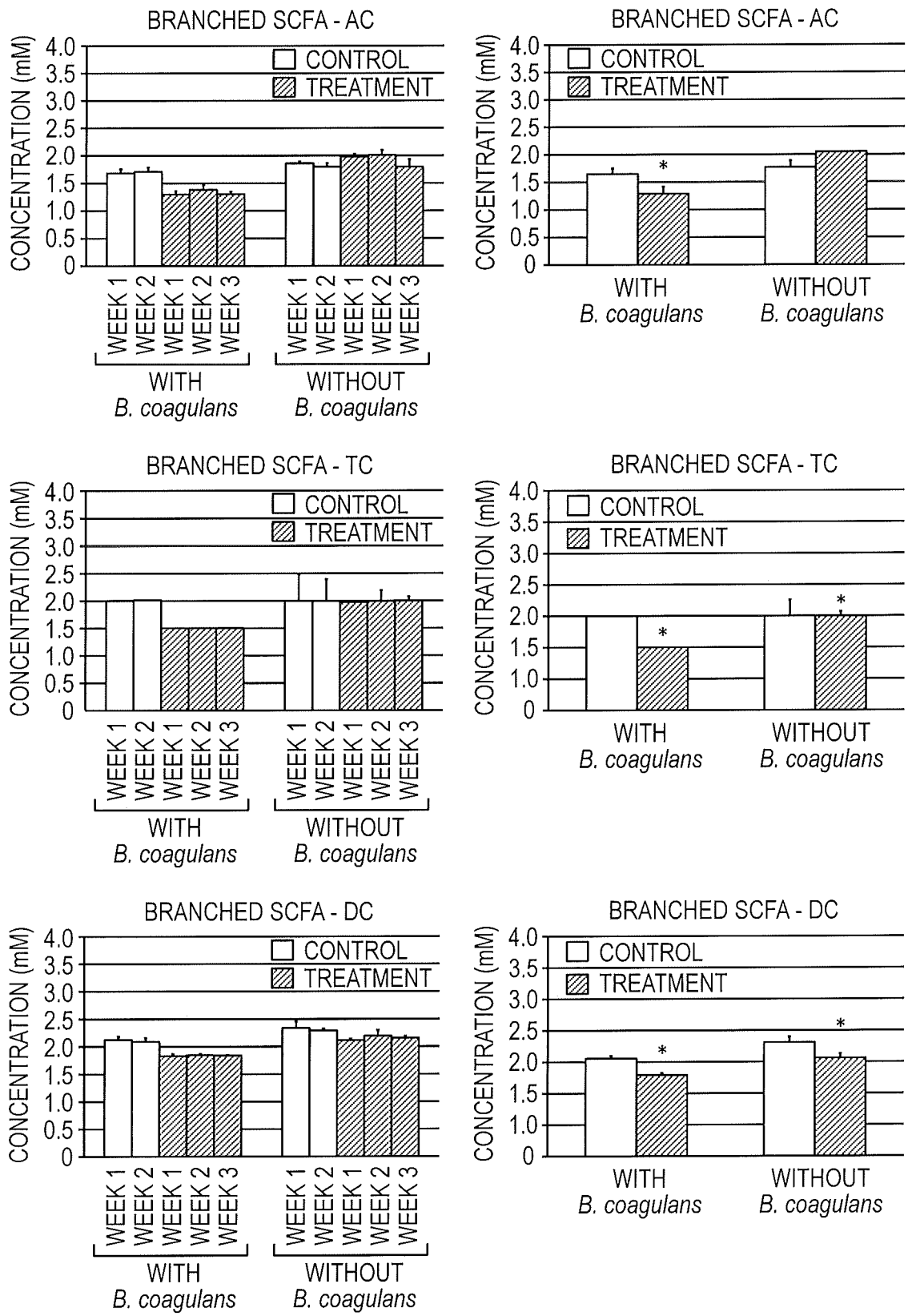
FIG. 8 depicts the effect of the multi-fiber compositions of the present invention on branched SCFA production in the ascending (AC; upper), transverse colon (TC; middle), and descending colon (DC; lower). Left: average weekly branched SCFA production during control or treatment weeks (n=3), right: average branched SCFA production over the control (n=6) and treatment period (n=9) (* indicates statistically significant differences).

The production of ammonium (NH4+) and branched SCFAs (sum of isobutyrate, isovalerate and isocaproate) typically result from protein degradation in the gut, and reflect proteolytic activity of the gut microbiota. Such increased activity has been associated with direct and indirect detrimental health effects (i.e., colon carcinogenesis), while a reduction in ammonium ion and SCFA production is considered beneficial. Results are depicted in FIG. 8. In the current experiments, it was shown that 1) SCFA and ammonium production decreased significantly during treatment with the multi-fiber composition with B. coagulans in all intestinal regions, and were maintained throughout the treatment periods; 2) treatment with the multi-fiber without B. coagulans was associated with decreased levels of ammonium ions only in the transverse and descending colon regions, while levels of SCFAs only decreased in the descending colon region. Reduction of ammonium ions and branched SCFA concentrations in all intestinal regions by the product with B. coagulans indicated that this composition had a positive effect on proteolytic fermentation. Similarly, the multi-fiber composition without B. coagulans significantly reduced ammonium ion concentrations in the transverse and descending colon vessels, while branched SCFA production was significantly reduced in the descending colon vessel. Considered together, these results indicated that both prebiotic compositions produced decreased proteolytic fermentation in the colon, demonstrating that the products tested were capable of producing health-promoting effects, consistent with effects reported by others for fibers.

Figure 9A:
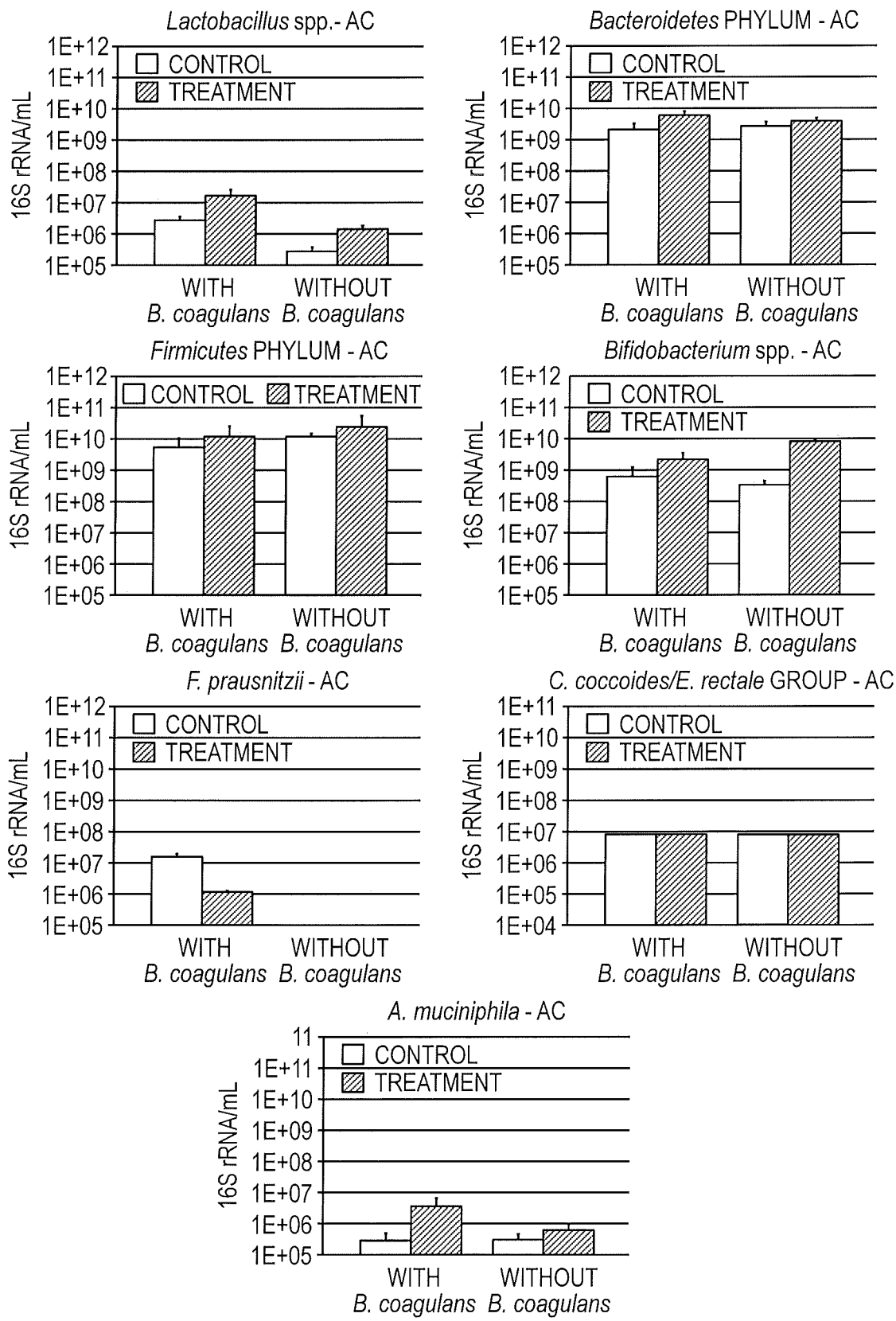
FIGS. 9A, 9B and 9C depict the effect of the multi-fiber compositions of the present invention on seven microbial populations in the ascending colon (AC.
Figure 9B:
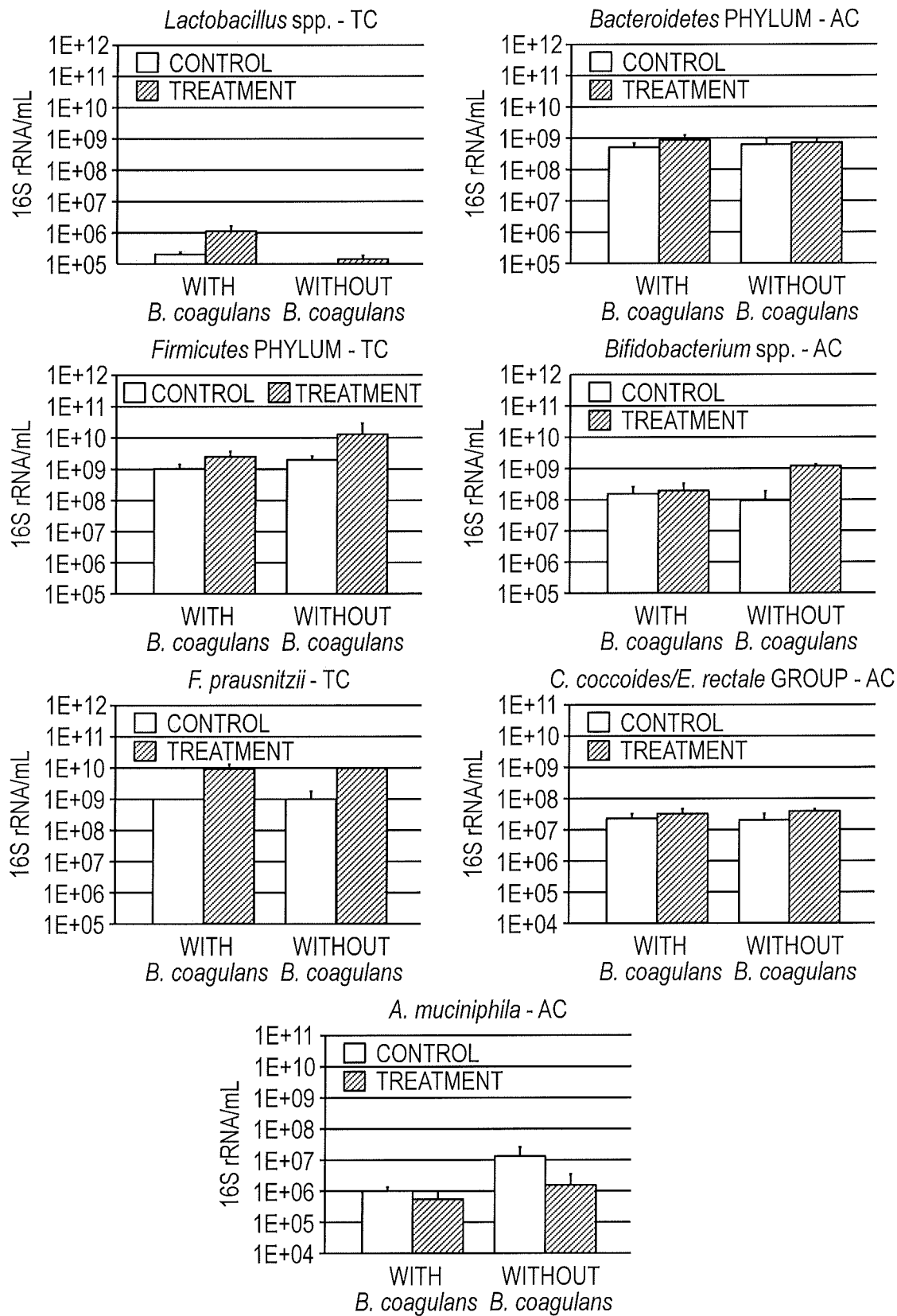
Figure 9C:
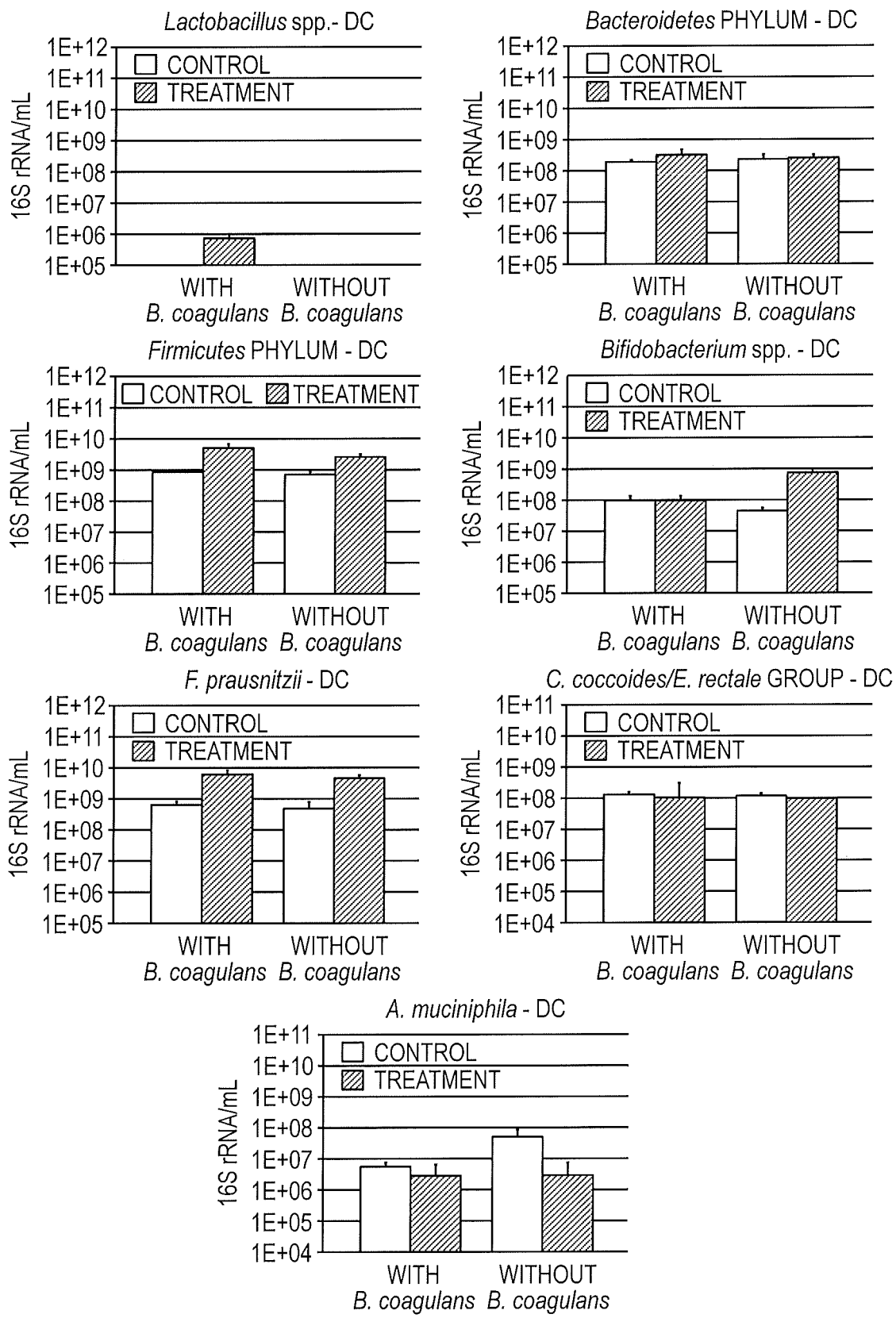

Analysis of Effects on the Microbiome Organism Populations. Quantitative PCR (qPCR) is a molecular technique that is based on the quantification of specific bacterial sequences (16S rRNA genes) through amplification. Through careful selection of selective primers, qPCR allows for direct targeted quantification of taxonomic groups of interest in a microbial ecosystem. The effects of the multi-fiber compositions of the instant invention on seven microbial populations in the ascending, transverse and descending colon vessels. Effects were assessed by comparing DNA copy numbers from the control period with those from the treatment period. With respect to monitoring levels of Lactobacilli, these bacteria are regarded as beneficial saccharolytic bacteria that are capable of producing high concentrations of lactate. Lactate is an important metabolite in the human colon environment because of its antimicrobial properties, but also because it is the driver of a series of trophic interactions with other bacteria, resulting in the production of downstream metabolites. Results showed that treatment of colon regions with both of the tested multi-fiber compositions stimulated growth of Lactobacillus spp. in each of the three colon regions. Like lactobacilli, bifidobacteria produce lactate, but they are also one of the primary acetate producers; effects on this bacterial population are often reflected in acetate production levels. While they are not capable of producing butyrate themselves, bifidobacteria can often stimulate butyrate production via cross-feeding interactions. Results of these experiments are shown in FIGS. 9A, 9B and 9C. Results showed that treatment with the multi-fiber composition without B. coagulans had a strong bifidogenic effect in all intestinal regions, while treatment with the composition with B. coagulans stimulated growth only in the ascending colon. These results were in line with the acetate and the butyrate production data (discussed supra), where the multi-fiber composition without B. coagulans was found to stimulate acetate and butyrate production in all intestinal regions, while the composition with B. coagulans had only a small effect. The phylum Bacteroidetes contains the most abundant propionate producers. Hence, in some cases a relationship can be found between propionate concentrations and the abundance of these organisms. Results showed that the multi-fiber composition with B. coagulans had a strong propiogenic effect. Yet, both compositions weakly stimulated growth of the bacteroidetes population, although the effects was greater with the composition that included the B. coagulans component. The phylum Firmicutes contains Clostridium clusters IV and XIVa, which are known to contain important butyrate producing organisms. While Faecalibacterium prausnitzii belongs to cluster IV, Clostridium coccoides (recently reclassified as Blautia coccoides) and Eubacterium rectale are both members of Clostridium cluster XIVa. Both multi-fiber prebiotic products stimulated growth of Firmicutes, which may be linked to the increases in butyrate production observed (discussed supra). Both compositions stimulated growth of F. prausnitzii to similar levels, which is likely linked to the increases in butyrate production. Further, F. prausnitzii is an indicator of intestinal health (Miguel, et al. (2013) Curr. Opin. Microbiol. 16:255-61), with demonstrated anti-inflammatory effects. Decreases in the abundance of F. prausnitzii have also been linked to dysbiosis. Neither of the compositions tested altered the abundance of B. coccoides and E. rectale. Both compositions stimulated growth of A. muciniphila in the ascending colon, but led to a slight reduction in copy numbers in the transverse and distal colon vessels.

Effects on Gut Wall Function. The last series of in vitro studies performed was directed to examining effects of the two multi-fiber compositions on functionality of the gut. Because bacteria closely interact with the gut wall, modulation of microbial activity and abundance by the multi-fiber prebiotics is likely to affect gut wall function. This was assessed by evaluating intestinal epithelial permeability and specific immune markers in vitro. Samples collected from the SHIME experiments were used to evaluate in vitro the effect of the fermented products on intestinal epithelial barrier function and immune markers. These included samples from the ascending, transverse and descending colon vessels that were collected at the end of the control and treatment periods for both of the test compositions (multi-fiber mixtures with and without B. coagulans).

A Caco-2 co-culture experiment was performed as previously described (Daguet, et al. (2016) J. Functional Foods 20:369-379). Briefly, Caco-2 cells (HTB-37; American Type Culture Collection) were seeded in 24-well semi-permeable inserts (0.4 μm pores size) at a density of $1\times10^5$/insert. Caco-2 cell monolayers were cultured for 14 days, with three medium changes/week, until a functional cell monolayer with a trans-epithelial electrical resistance (TEER) of more than 300'Ω/cm² was obtained. Cells were maintained in Dulbecco's Modified Eagle Medium (DMEM) containing 25 mM glucose and 4 mM glutamine and supplemented with 10 mM HEPES and 20% (v/v) heat-inactivated (HI) fetal bovine serum (FBS). THP1-Blue (InvivoGen) cells were maintained in Roswell Park Memorial Institute (RPMI) 1640 medium containing 11 mM glucose and 2 mM glutamine and supplemented with 10 mM HEPES, 1 mM Sodium pyruvate and 10% (v/v) HI-FBS. THP1-Blue are THP1 human monocytes stably transfected with a reporter construct expressing a secreted alkaline phosphatase (SEAP) gene under the control of a promoter inducible by the transcription factor NF-κB. Upon TLR activation by molecules such as LPS (isolated from Gram-negative bacteria), NF-κB becomes activated and induces the expression and secretion of SEAS. This is then measured in the supernatant by using the QUANTI-Blue reagent (InvivoGen). THP1-Blue cells were seeded in 24-well plates at a density of $5 \times 10^5$ cells/well and treated with 100 ng/mL of PMA for 48 hours. PMA induces the differentiation of the cells into macrophage-like cells that able to adhere and are primed for TLR signaling.

Before co-culture, the TEER of the Caco-2 monolayers was measured by using an Epithelial Volt-Ohm meter. The TEER of an empty insert was subtracted from all readings to account for the residual electrical resistance of an insert. Then, the Caco-2-bearing inserts were placed on top of the PMA-differentiated THP1-Blue cells for further experiments, as previously described (Possemiers, et al. (2013) *J. Agric. Food Chem.* 61:9380-9390); Daguet, supra). The apical compartment (containing the Caco-2 cells) was filled with sterile-filtered (0.22 μm) colonic SHIME suspensions (diluted 1:5 (v/v) in Caco-2 complete media). Cells were also treated apically with sodium butyrate (NaB; 12 mM) as a positive control. The basolateral compartment (containing the THP1-Blue cells) was filled with Caco-2 complete media. Cells were also exposed to Caco-2 complete media in both chambers as control. Cells were treated for hours, after which the TEER was measured. After subtracting the TEER of the empty insert, all 24-hour values were normalized to their own value (to account for the differences in TEER of the different inserts) and were presented as percentage of the initial value. Then, the basolateral supernatant was discarded and cells were stimulated basolaterally with Caco-2 complete media containing 500 ng/mL of ultrapure LPS (*Escherichia coli* K12, InvivoGen). Cells were also stimulated basolaterally with LPS and hydrocortisone (HC; 1 μM) and media without LPS (LPS−) as controls. After 6 hours of LPS stimulation the basolateral supernatant was collected for measurement of cytokines (human IL-1p, IL-6, IL-8, IL-10, TNF-α, CXCL10 and MCP-1 by Luminex multiplex (Affymetrix-eBioscience) and for assessing NF-κB activity, according to the manufacturers' instructions. All treatments were done in triplicate. Cells were incubated at 37° C. in a humidified atmosphere of air/CO2 (95:5, v/v).

The paracellular (intercellular) transport of Lucifer yellow (LY; MW 457) was performed under the same conditions as described above for cytokines measurement; the difference between the two experiments occurs after 24 hours of pre-treatment; then, instead of LPS, cells were given LY on the apical side. Briefly, after 24 h pre-treatment with SHIME® suspensions and NaB (12 mM), both apical and basolateral supernatants were discarded and the cells washed and equilibrated in transport media (Hanks' Balanced Salt Solution (HBSS) supplemented with 10 mM HEPES) for 30 minutes at 37° C. Then, the apical chamber was filled with 100 μM LY/insert diluted in transport media. The basolateral chamber was filled with transport media only. The transport of LY across the monolayer of Caco-2 cells was measured on the basolateral side after 24 h (fluorescence measured at 485 nm excitation/528 nm emission).

The results obtained for the controls (CM and NaB) on permeability markers (TEER and LY paracellular transport) showed that after 24 hours of co-culture incubation, the complete media (CM) control showed a nearly 50% decrease in TEER due to the damage induced by the PMA-activated THP1 cells on Caco-2 cells. As expected, Sodium butyrate (NaB; a positive control) was able to protect Caco-2 cells from this damage. However, this difference between treatments was not seen in the LY transport experiment, possibly because, despite the TEER decrease observed in the CM control, the transport of small molecules was still not greatly affected.

The results obtained in controls for the different immune markers showed that, as expected, LPS was able to increase the secretion of all immune markers. In contrast, hydrocortisone (HC), acted as a broad immunosuppressant by dampening LPS-induced cytokine and chemokine levels, and also by inhibiting LPS-induced transcriptional activity of NF-κB. In contrast, NaB had marker-dependent effects. Although NaB increased the transcriptional activity of NF-κB, it had clear selective post-transcriptional inhibitory activities on some immune mediators, such as IL-1β and TNF-α. Thus, the control, NaB, was shown to selectively increase LPS-induced IL-10 and IL-6 (involved in immune homeostasis) and to selectively inhibit LPS-induced and TNF-α (pro-inflammatory cytokines) and CXCL10, MCP-1 and IL-8 (chemokines involved in recruitment of immune cells). These control results, considered together, validated the test systems for use in examining the effects of the multi-fiber mixtures of the present invention.

Figure 10:
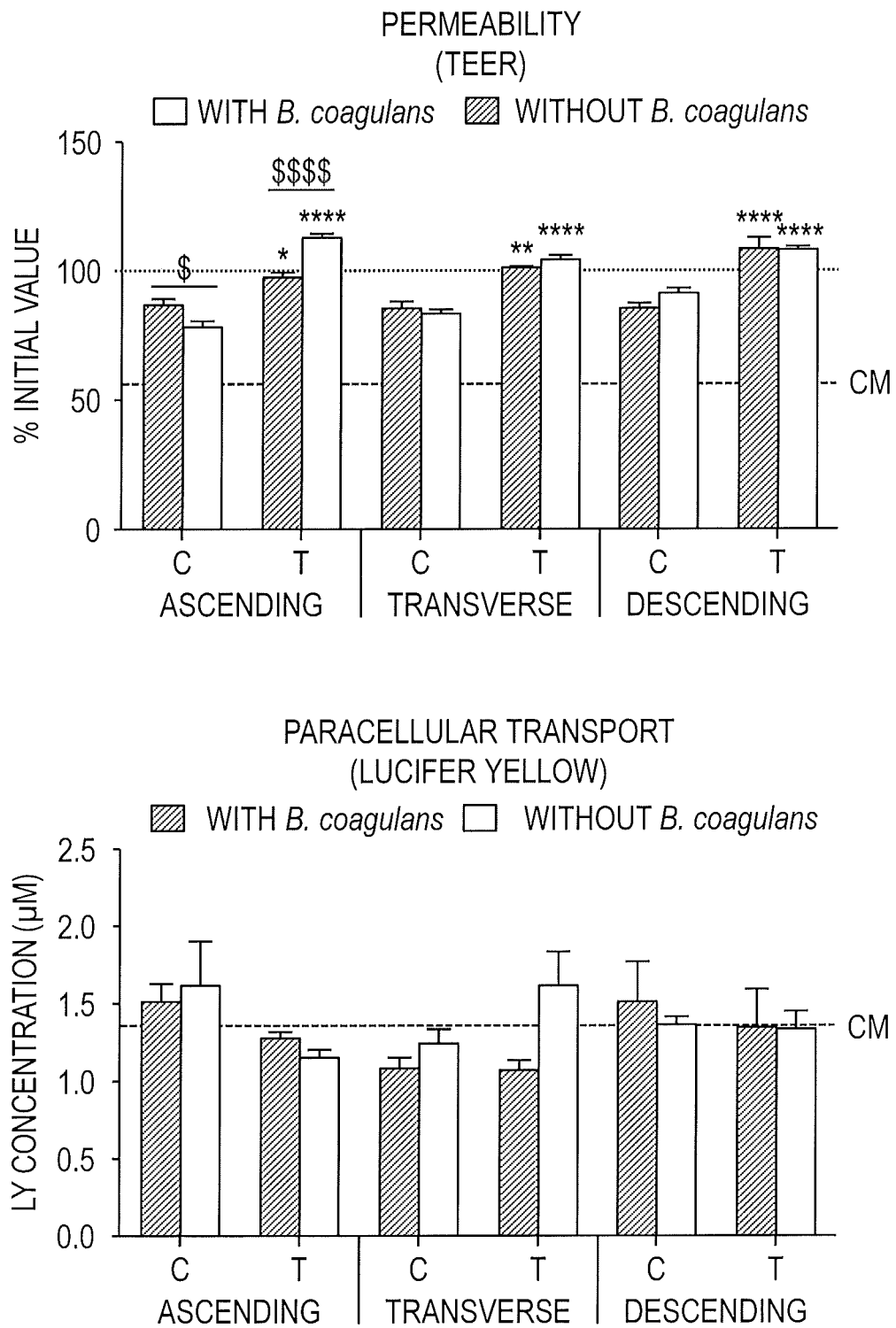
FIG. 10 depicts the effect of the SHIME-collected samples on transepithelial electrical resistance (TEER, upper panel) and paracellular transport of Lucifer yellow (LY) on the Caco-2/THP1-Blue co-cultures (lower panel). TEER was measured 24 h after pre-treatment of the co-cultures and each 24 h value was normalized to its corresponding 0 h value and is shown as percentage of initial value. The upper dotted line represents 100% (initial value). The transport of LY is measured after 48 h of co-culture (24 h pre-treatment+24 h LY). The lower dashed line depicted in both plots corresponds to the experimental control CM (complete media). (*) represents statistical significant differences between C and T within each product. ($) represents statistical significant differences between the multi-fiber compositions of the present invention. C: SHIME control sample; T: SHIME treatment sample.

The samples collected from the last weeks of control and treatment from all colon vessels were diluted in Caco-2 complete media after filtration and were given apically to the co-cultures for 24 hours. When compared to the complete media (CM) control results, all samples, including the SHIME controls, are able to maintain the TEER. However, the multi-fiber treatment samples were shown to more effective, maintaining the TEER at levels close to or above 100% (FIG. 10). This result was statistically significant for both multi-fiber compositions, for all colon vessels. When comparing the two compositions, only the ascending colon samples were significantly different between the compositions with and without *B. coagulans*, with the TEER shown to be higher with the composition treatment that contained *B. coagulans*. Concerning the transport of LY, the results indicated that the passive transport of small molecules was not greatly affected by either treatment (FIG. 10). However, when compared to the respective controls, both the ascending and descending colon samples collected during treatment seem to slightly decrease the transport of LY, although the changes were not statistically significant.

Figure 11:
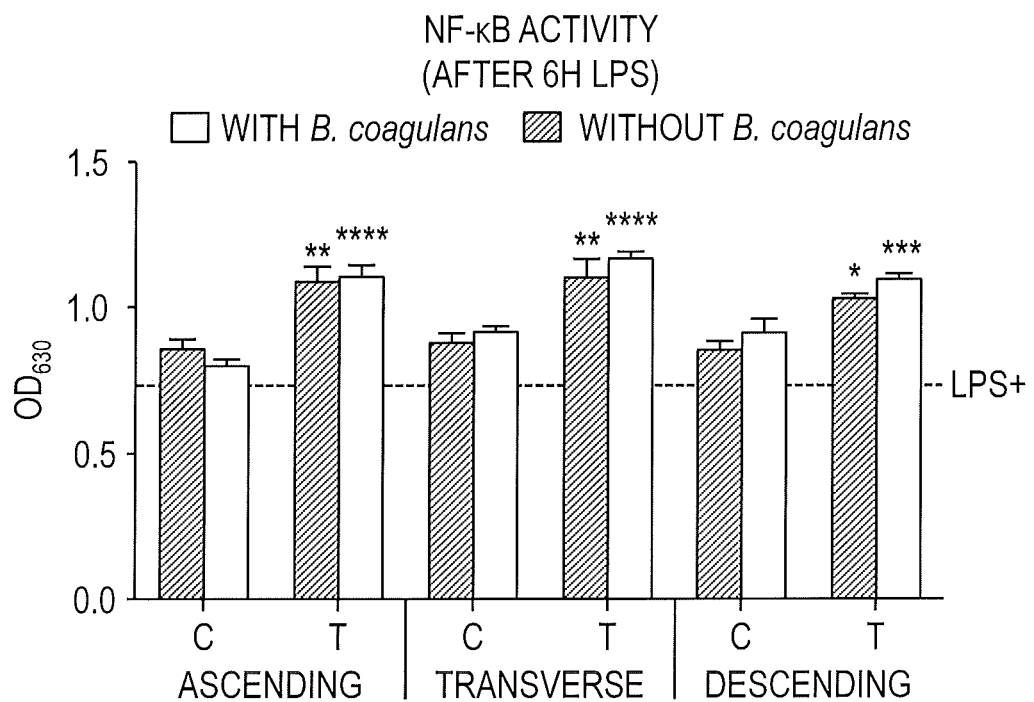
FIG. 11 depicts the effect of the SHIME-collected samples on NF-κB activity of THP1-Blue cells. NF-κB activity levels were measured after 6 h of LPS treatment of the co-cultures that were first pre-treated for 24 h with SHIME-collected samples. The red dashed line corresponds to the experimental control LPS+. (*) represents statistical significant differences between C and T within each product. No statistical significant differences were found between the two multi-fiber compositions of the present invention. C: SHIME control sample; T: SHIME treatment sample.

After 24 hours of pre-treatment of the Caco-2/THP1-Blue co-cultures with SHIME® samples, the basolateral supernatant was discarded and the cells stimulated with LPS. After 6 hours of stimulation, the basolateral supernatant was collected to measure cytokines and chemokines and to determine NF-κB activity levels. When compared to the LPS+ control, all samples, including the controls, increased or potentiated LPS-induced NF-κB transcriptional activity. However, this increase, which was seen for all vessels, and for both compositions, was significantly higher in the treated SHIME® samples when compared to the control samples (FIG. 11). There was no significant difference between the two multi-fiber compositions tested.

Figure 12:
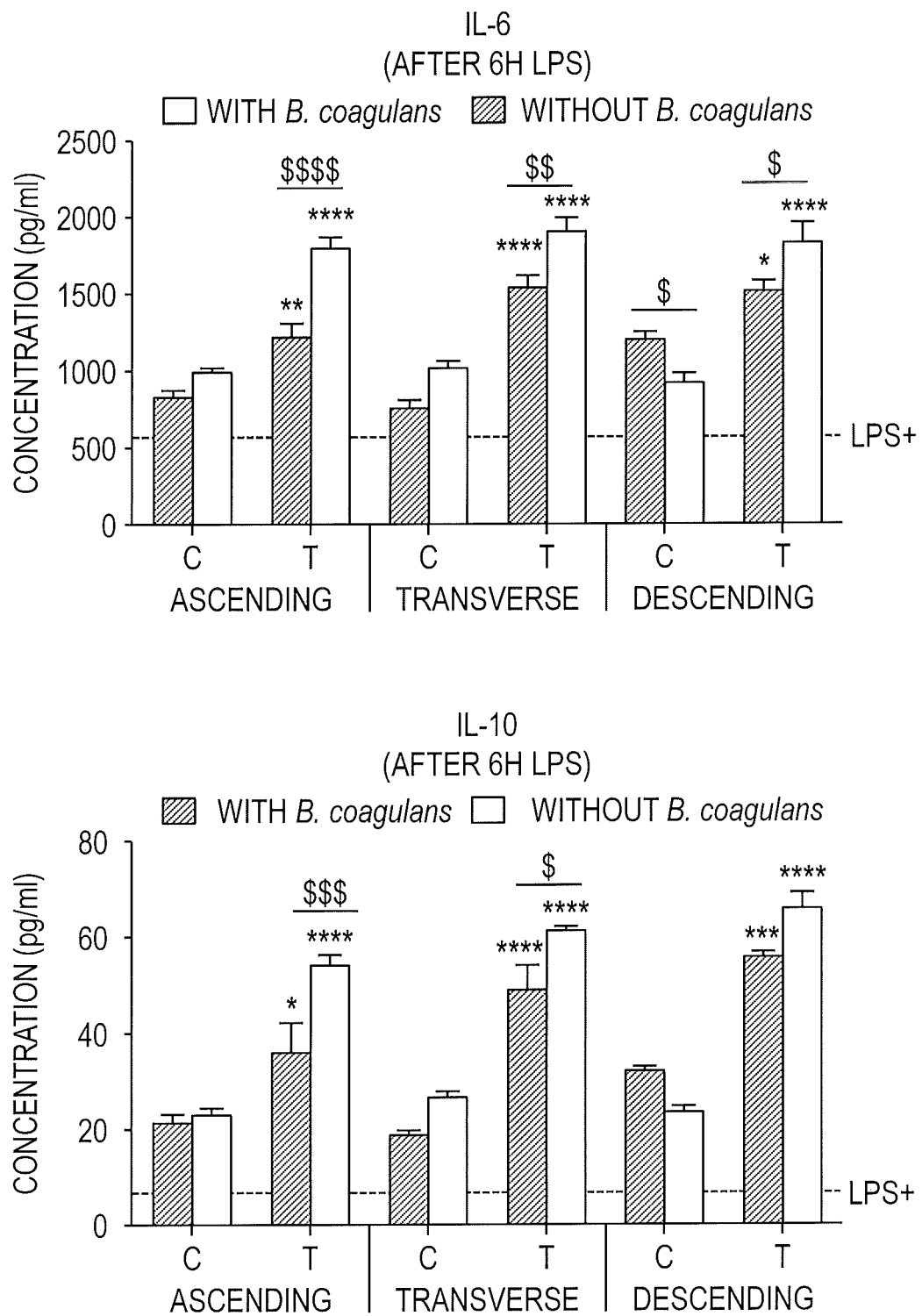
FIG. 12 depicts the effect of the SHIME-collected samples on IL-6 (upper panel) and IL-10 (lower panel) levels. Cytokine levels were measured after 6 h of LPS treatment of the co-cultures that were first pre-treated for 24 h with SHIME-collected samples. The dashed line corresponds to the experimental control LPS+. (*) represents statistical significant differences between C and T within each product. ($) represents statistical significant differences between the multi-fiber compositions of the present invention. C: SHIME control sample; T: SHIME treatment sample.

The results observed for NF-κB activity were reflected in the results obtained for IL-6 and IL-10 levels (FIG. 12). Similar to the results obtained for NF-κB activity, all SHIME®-collected samples (both control and treatment) increased or potentiated LPS-induced IL-6 and IL-10 levels. However, this increase was more prominent in the cells exposed to the treated with the multi-fiber compositions.

When compared to the respective controls, the multi-fiber treated samples collected from SHIME® significantly increased levels of IL-6 and IL-10, an effect observed in all three colon vessels. There was a difference in the magnitude of the effect between the two multi-fiber compositions, however; there were higher levels of the cytokines observed in colon vessels treated with the multi-fiber mixture containing B. coagulans as a component in all of the colon vessels. All SHIME® samples, including the controls, appeared to increase or potentiate LPS-induced IL-1β, while LPS-induced TNF-α levels were inhibited. When compared to the respective SHIME controls, the multi-fiber composition treated samples appeared to induce a smaller increase in IL-1β levels and to inhibit TNF-α levels to a greater extent. Greater activity was seen in transverse colon samples treated with the multi-fiber composition without B. coagulans with respect to IL-1β and in transverse colon samples treated with the B. coagulans component with respect to TNF-α.

All SHIME® samples, including the controls, inhibited LPS-induced CXCL10, an effect which appeared to be more pronounced in the samples treated with the compositions of the present invention. Concerning IL-8 levels, the effects were weak.

Figure 13:
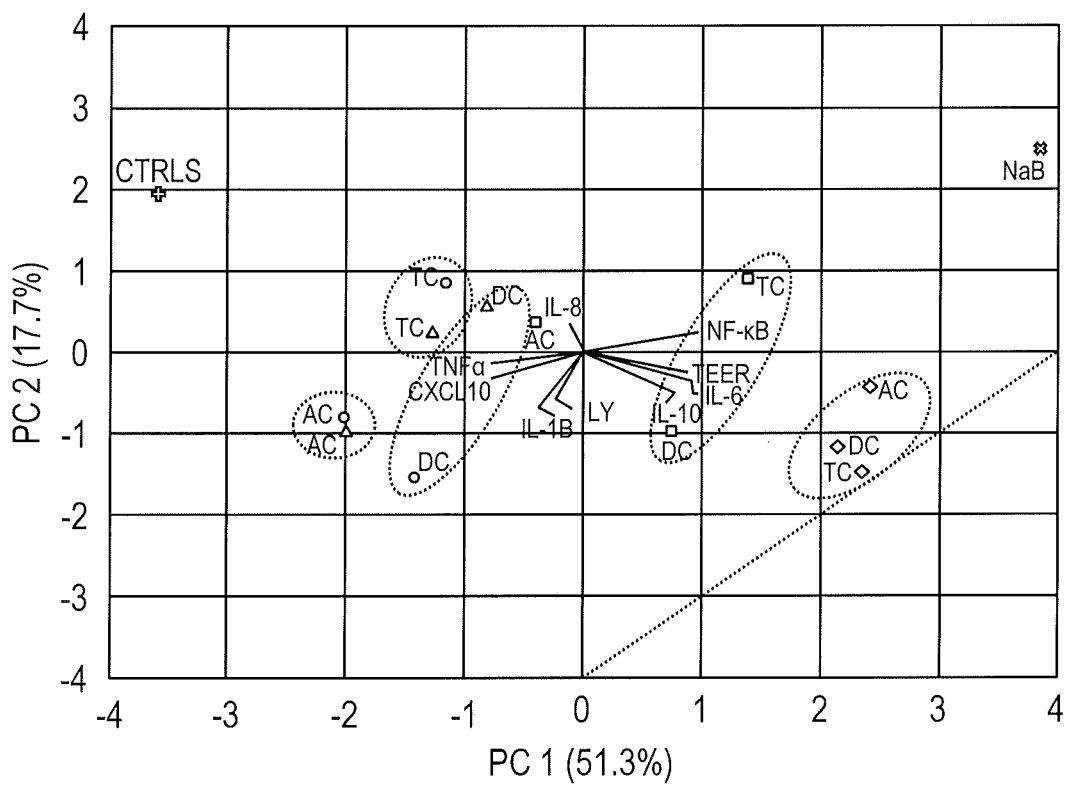
FIG. 13 depicts a joint PCA/Correlation biplot showing the similarity between observations and correlation between variables. The biplot plots variables as vectors and observations as symbols. In the biplot 1) the controls complete media (CM) and LPS+ were reduced to 1.0 and are depicted as one single point ("+", Ctrls); 2) NaB ("x"); 3) the control period of the multi-fiber composition without *B. coagulans* (circle); 4) the control period of the multi-fiber composition with *B. coagulans* (triangle); 5) the treatment period of the multi-fiber composition without *B. coagulans* (square); and 6) the treatment period of the multi-fiber composition with *B. coagulans* (diamond).

Because the number of measured variables and samples tested in these experiments was relatively high, an analysis that reduces complexity can be useful for interpretation of results. Therefore, a joint PCA/Correlation biplot was made (FIG. 13).

The data, when reduced to two components, is explained by the first two components by approximately 69%, where the first component accounts for nearly 51% of the variance in the original 9 variables. The variables that mostly contribute to the first component are TEER, NF-κB, IL-6, TNF-α and CXCL10, whereas LY, IL-1β and IL-8 contribute mostly to the second component.

Considered together, the SHIME® experimental data demonstrated that both multi-fiber products were easily fermented in a human colonic environment, resulting in the formation of end products that are expected to positively affect the human gut environment. Additionally, both multi-fiber products, with and without B. coagulans as a component, exhibited activity consistent with beneficial effects on human health.

What is claimed is:

1. A composition for improving or maintaining digestive health, immunity, short chain fatty acid levels in the colon, weight and glucose balance comprising xylooligosaccharide, arabinogalactan, inulin, Ganoderma lucidum beta glucan, insoluble yeast β(1,3/1,6)-glucan, oat β(1,3/1,4)-glucan, insoluble dried Saccharomyces cerevisiae fermentate, and 2% to 10% by weight Bacillus coagulans.

2. The composition of claim 1, wherein the yeast comprises Saccharomyces cerevisiae.

3. The composition of claim 1, further comprising at least one excipient.

4. The composition of claim 1, wherein the composition comprises a food product, dietary supplement, comestible medical food, pharmaceutical product, or nutraceutical product.

5. A composition for improving or maintaining digestive health, immunity, short chain fatty acid levels in the colon, weight and glucose balance consisting essentially of xylooligosaccharide, arabinogalactan, inulin, Ganoderma lucidum beta glucan, insoluble yeast β(1,3/1,6)-glucan, oat β(1,3/1,4)-glucan, insoluble dried Saccharomyces cerevisiae fermentate, and 2% to 10% by weight Bacillus coagulans.

6. A method for improving or maintaining digestive health, immunity, short chain fatty acid levels in the colon, weight and glucose balance comprising administering to a subject in need of treatment an effective amount of a composition comprising xylooligosaccharide, arabinogalactan, inulin, Ganoderma lucidum beta glucan, insoluble yeast β(1,3/1,6)-glucan, oat β(1,3/1,4)-glucan, insoluble dried Saccharomyces cerevisiae fermentate, and 2% to 10% by weight Bacillus coagulans so that the subject's digestive health, immunity, short chain fatty acid levels in the colon, weight and glucose balance is improved or maintained.

7. The composition of claim 1, wherein the short chain fatty acid is propionate, butyrate or a combination thereof.

8. The composition of claim 5, wherein the short chain fatty acid is propionate, butyrate or a combination thereof.

9. The method of claim 6, wherein the short chain fatty acid is propionate, butyrate or a combination thereof.

10. The composition of claim 1, wherein the composition provides an amount of Bacillus coagulans in the range of amount of 1.0 to 5.0 billion CFU.

11. The composition of claim 5, wherein the composition provides an amount of Bacillus coagulans in the range of amount of 1.0 to 5.0 billion CFU.

12. The method of claim 6, wherein the composition provides an amount of Bacillus coagulans in the range of amount of 1.0 to 5.0 billion CFU.

* * * * *